(12) United States Patent
Burleigh et al.

(10) Patent No.: US 8,923,535 B2
(45) Date of Patent: Dec. 30, 2014

(54) MAGNETOSTRICTIVE AUDITORY SYSTEM

(71) Applicant: Brain Basket, LLC, Boulder, CO (US)

(72) Inventors: Joan Billger Burleigh, Boulder, CO (US); Joan Phillips Waldron, Boulder, CO (US)

(73) Assignee: Brain Basket, LLC, Boulder, CO (US)

( * ) Notice: Subject to any disclaimer, the term of this patent is extended or adjusted under 35 U.S.C. 154(b) by 0 days.

(21) Appl. No.: 13/749,822

(22) Filed: Jan. 25, 2013

(65) Prior Publication Data
US 2013/0190550 A1 Jul. 25, 2013

Related U.S. Application Data

(62) Division of application No. 12/500,681, filed on Jul. 10, 2009, now Pat. No. 8,363,862.

(60) Provisional application No. 61/080,180, filed on Jul. 11, 2008.

(51) Int. Cl.
| | |
|---|---|
| *H04R 25/00* | (2006.01) |
| *A61N 2/00* | (2006.01) |
| *H04R 15/00* | (2006.01) |
| *A61N 2/02* | (2006.01) |

(52) U.S. Cl.
CPC ............... *A61N 2/006* (2013.01); *H04R 15/00* (2013.01); *H04R 25/00* (2013.01); *A61N 2/02* (2013.01)
USPC ........... 381/190; 381/312; 381/326; 381/328; 600/25; 607/55; 607/56; 607/57

(58) Field of Classification Search
USPC ......... 381/190, 312, 326, 328, 331, 151, 380, 381/400; 600/25; 607/55, 56, 57
See application file for complete search history.

(56) References Cited

U.S. PATENT DOCUMENTS

| | | | |
|---|---|---|---|
| 1,889,153 A | * | 11/1932 | Pierce .......................... 381/163 |
| 2,063,944 A | | 12/1936 | Pierce |
| 2,791,732 A | | 5/1957 | Jones |

(Continued)

FOREIGN PATENT DOCUMENTS

| | | |
|---|---|---|
| EP | 1439737 | 7/2004 |
| WO | 9414293 | 6/1994 |
| WO | 9621333 | 7/1996 |
| WO | 2007044460 | 4/2007 |

OTHER PUBLICATIONS

U.S. Appl. No. 61/080,180, filed Jul. 11, 2008, by Joan M. Burleigh.

(Continued)

*Primary Examiner* — Davetta W Goins
*Assistant Examiner* — Amir Etesam
(74) *Attorney, Agent, or Firm* — William W. Cochran; Cochran Freund & Young LLC

(57) ABSTRACT

Disclosed is hearing device that uses magnetostrictive materials to assist a user in hearing and comprehending sounds. Conductive coils are made with a magnetostrictive covering that can comprise a film or other coating. In addition, printed circuit boards can be used with traces that form a coil to generate a magnetic field that activates a magnetostrictive film disposed over the coil traces on the printed circuit board. Enhanced effects are achieved using these systems. Delays in the signal processing can also be introduced by varying the thickness of the magnetostrictive coverings.

8 Claims, 22 Drawing Sheets

(56) References Cited

U.S. PATENT DOCUMENTS

| | | |
|---|---|---|
| 3,774,134 A | 11/1973 | Kardashian et al. |
| 3,968,693 A | 7/1976 | Kazahaya |
| 4,236,230 A | 11/1980 | Thompson |
| 4,499,515 A | 2/1985 | Piotrowski et al. |
| 4,520,413 A | 5/1985 | Piotrowski et al. |
| 4,606,329 A | 8/1986 | Hough |
| 4,716,556 A | 12/1987 | Raskin et al. |
| 4,776,322 A | 10/1988 | Hough et al. |
| 4,904,233 A | 2/1990 | Hakansson et al. |
| 5,015,225 A | 5/1991 | Hough et al. |
| 5,176,620 A | 1/1993 | Gilman |
| 5,258,707 A | 11/1993 | Begin et al. |
| 5,260,615 A | 11/1993 | Sahashi et al. |
| 5,338,287 A | 8/1994 | Miller et al. |
| 5,455,842 A | 10/1995 | Mersky et al. |
| 5,729,131 A | 3/1998 | Begin |
| 6,137,889 A | 10/2000 | Shennib et al. |
| 6,176,943 B1 | 1/2001 | Wun-Fogle et al. |
| 6,940,989 B1 | 9/2005 | Shennib et al. |
| 7,250,839 B2 | 7/2007 | Racz |
| 2002/0035309 A1 | 3/2002 | Leysieffer |
| 2004/0234092 A1 | 11/2004 | Wada et al. |
| 2005/0020873 A1 | 1/2005 | Berrang et al. |
| 2005/0113633 A1 | 5/2005 | Blau et al. |
| 2006/0029248 A1 | 2/2006 | Waldron |
| 2007/0041595 A1 | 2/2007 | Carazo et al. |
| 2007/0083078 A1 | 4/2007 | Easter et al. |
| 2007/0108973 A1 | 5/2007 | Lanning et al. |

OTHER PUBLICATIONS

U.S. Appl. No. 11/443,859, filed May 31, 2006, entitled "Apparatus and Methods for Mitigating Impairments Due to Central Nervous System Binaural Phase-Time Asynchrony".

International Search Report and Written Opinion mailed Sep. 15, 2009, in PCT Application Serial No. PCT/US2009/050288.

* cited by examiner

MAGNETOSTRICTIVE AUDITORY SYSTEM

CROSS-REFERENCE TO RELATED APPLICATION

This application is a divisional application of U.S. patent application Ser. No. 12/500,681, entitled "Magnetostrictive Auditory System," filed Jul. 10, 2009, by Joan M. Burleigh et al., which application claims benefit of and priority to U.S. Provisional Patent Application Ser. No. 61/080,180, entitled "Magnetostrictive Auditory System" by Joan M. Burleigh, et al., filed Jul. 11, 2008, the entire contents of which are specifically incorporated herein by reference for all that they disclose and teach.

BACKGROUND OF THE INVENTION

Portable hearing devices have been very effective in assisting individuals that have impaired hearing and/or comprehension in difficult listening environments to more clearly hear, understand and enjoy auditory signals. Depending upon the type of impairment that an individual may have, or the environment in which the individual may have difficulty hearing, hearing devices may operate more efficiently with some individuals and not as well with others. Many of the problems associated with hearing loss as well as comprehension of audible signals are not well understood. A large number of factors can affect both hearing and comprehension of various types of audible signals. As a result, hearing devices that aid a user in hearing and comprehending audible signals may not be simply dependent upon amplification of the audible signal at specified frequencies.

SUMMARY OF THE INVENTION

An embodiment of the present invention may therefore comprise a method of assisting an individual with auditory comprehension of audible signals using a hearing device comprising: coating a conductive wire with a magnetostrictive coating; forming the wire in a coil; generating an electrical signal from the auditory signal; applying the electrical signal to the coil that causes the magnetostrictive coating to change size in response to the electrical signal so that the magnetostrictive coating generates auditory vibrations to assist the individuals with the auditory comprehension of audible sounds.

An embodiment of the present invention may therefore further comprise a hearing device that assists users having impaired auditory comprehension comprising: a detector that detects audible signals and translates the audible signals into an electrical signal that varies in amplitude in accordance with the audible signals; a driver that amplifies the electrical signal to provide an amplified electrical signal; a conductive wire formed in a coil that is connected to the driver to receive the amplified electrical signal and generate a magnetic wave in response to the electrical signal that varies in amplitude in accordance with the amplitude of the electrical signal; a first magnetostrictive coating substantially surrounding the conductive wire that changes size in response to the electrical signal and generates auditory vibrations corresponding to the amplitude of the electrical signal that assist the users in comprehending the audible signals.

An embodiment of the present invention may therefore further comprise a method of assisting an individual with auditory comprehension of audible signals using a hearing device comprising: forming a coil from a printed circuit board trace on a printed circuit board; covering the coil formed on the printed circuit board with a magnetostrictive film; generating an electrical signal from the auditory signal; applying the electrical signal to the coil that causes the magnetostrictive film to change size in response to the electrical signal so that the magnetostrictive film generates auditory vibrations to assist the individual with the auditory comprehension of audible signals.

An embodiment of the present invention may therefore further comprise a hearing device that assists users having impaired auditory comprehension comprising: a microphone that detects auditory signals and translates the auditory signals into an electrical signal that varies in amplitude in accordance with the auditory signals; a driver that amplifies the electrical signal to provide an amplified electrical signal; a coil formed from a printed circuit board trace on a printed circuit board; a first magnetostrictive film substantially covering the coil on the printed circuit board that changes size in response to a magnetic field generated by the amplified electrical signal that is applied to the coil and generates auditory vibrations corresponding to the amplitude of the amplified electrical signal that assist the users in comprehending the audible signals.

An embodiment of the present invention may therefore further comprise a method of assisting an individual with hearing an auditory signal using a hearing device comprising: coating a conductive wire with a magnetostrictive coating; forming the wire in a coil; generating an electrical signal from the auditory signal; applying the electrical signal to the coil that causes the magnetostrictive coating to change size in response to a magnetic field generated by the coil in response to the electrical signal so that the magnetostrictive coating generates auditory vibrations that assist the individual with hearing the auditory signal.

An embodiment of the present invention may therefore further comprise a hearing device that assists users having impaired auditory function comprising: a microphone that detects auditory signals and translates the auditory signals into an electrical signal that varies in amplitude in accordance with the auditory signals; a driver that amplifies the electrical signal to provide an amplified electrical signal; a conductive wire formed in a coil that is connected to the driver to receive the amplified electrical signal and generate a magnetic field in response to the electrical signal that varies in amplitude in accordance with the amplitude of the electrical signal; a first magnetostrictive coating substantially surrounding the conductive wire that changes size in response to the magnetic field and generates auditory vibrations corresponding to the amplitude of the amplified electrical signal that assist the users in hearing the auditory signals.

An embodiment of the present invention may therefore further comprise a method of assisting an individual with hearing auditory signals using a hearing device comprising: forming a coil from a printed circuit board trace on a printed circuit board; covering the coil formed on the printed circuit board with a magnetostrictive film; generating an electrical signal from the auditory signal; applying the electrical signal to the coil that causes the magnetostrictive film to change size in response to the electrical signal so that the magnetostrictive film generates auditory vibrations to assist the individuals with hearing the auditory signals.

An embodiment of the present invention may therefore further comprise a hearing device that assists users having impaired hearing comprising: a detector that detects auditory signals and translates the auditory signals into an electrical signal that varies in amplitude in accordance with the auditory signals; a driver that amplifies the electrical signal to provide an amplified electrical signal; a coil formed from a printed circuit board trace on a printed circuit board; a magnetostrictive film substantially covering the coil on the printed circuit board that changes size in response to a magnetic field generated by the amplified electrical signal that is applied to the coil and generates auditory vibrations corresponding to the amplitude of the amplified electrical signal that assist the users in hearing the auditory signals.

An embodiment of the present invention may therefore further comprise a method of assisting an individual with auditory comprehension and hearing of audible signals using a hearing device comprising: providing a diaphragm comprising a plastic and magnetostrictive material; forming a wire in a coil; mounting the diaphragm adjacent to the coil; generating an electrical signal from the auditory signal; applying the electrical signal to the coil that causes the magnetostrictive material to change size in response to a magnetic field generated by the electrical signal applied to the coil so that the magnetostrictive material generates auditory vibrations to assist the individuals with the auditory comprehension of audible sounds.

An embodiment of the present invention may therefore further comprise a hearing device that assists users having impaired auditory comprehension and hearing comprising: a detector that detects audible signals and translates the audible signals into an electrical signal that varies in amplitude in accordance with the audible signals; a driver that amplifies the electrical signal to provide an amplified electrical signal; a coil formed from a conductive wire that is connected to the driver to receive the amplified electrical signal and generate a magnetic field in response to the electrical signal that varies in amplitude in accordance with the amplitude of the electrical signal; a first diaphragm comprising a plastic and magnetostrictive material, the diaphragm mounted adjacent to the coil so that magnetic flux lines of the magnetic field cause the magnetostrictive material to change size and generate auditory vibrations in the diaphragm that correspond to the amplitude of the electrical signal that assist the users in comprehending and hearing the audible signals.

DETAILED DESCRIPTION OF THE EMBODIMENTS

Figure 1:
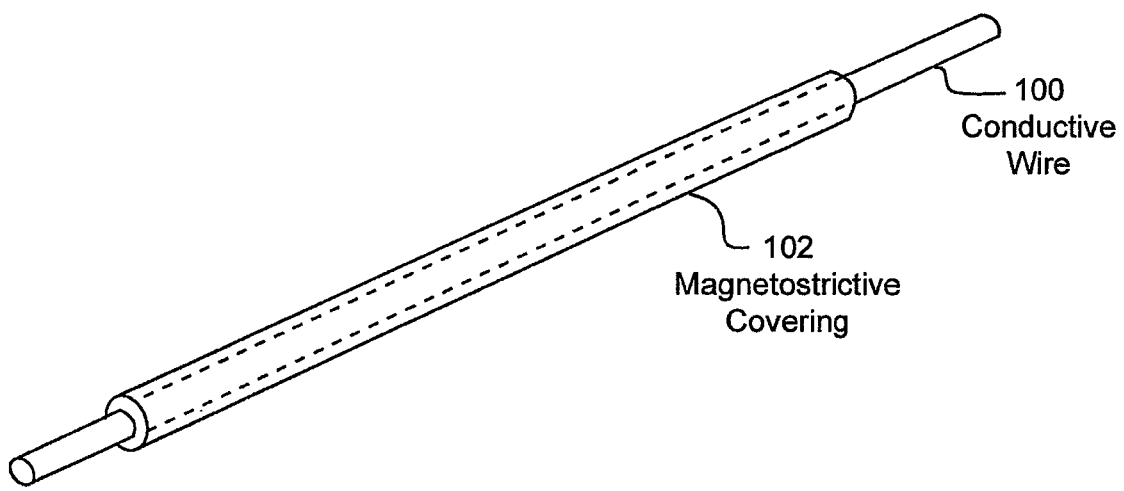
FIG. 1 is a schematic illustration of one embodiment of a conductive wire covered with a magnetostrictive covering.

FIG. 1 is a schematic illustration of a conductive wire 100 that is covered by a magnetostrictive covering 102. The magnetostrictive covering can comprise any of the magnetostrictive materials. For example, the magnetostrictive covering 102 may be a magnetostrictive film, an amorphous metallic alloy, a metallic glass, a metallic ribbon, a glassy metal, a ribbon alloy, a shaped memory alloy, a metallic foil, a metallic polymer or other materials and shapes. In addition, metallic polymers can be extruded over the conductive wire 100 using standard extrusion techniques for placing covers over wires to form the magnetostrictive covering 102. Magnetostrictive materials convert magnetic energy into kinetic energy, or the reverse, and are typically used to build actuators and sensors. Magnetostrictive properties can be quantified by the magnetostrictive coefficient (L), which is the fractional change in length as the magnetization of the material increases from zero to a saturation value.

Cobalt exhibits the largest room temperature magnetostriction of a pure element at 60 microstrain. Among alloys, the highest known magnetostriction is exhibited by Terfenol-D. Terfenol-D is represented as ThxDyl-xFe2. Terfenol-D exhibits approximately 2,000 microstrains in a field of 2 kOe (160 kA/m) at room temperature. Terfenol-D is the most widely used magnetostrictive material. As indicated above, it can be used as an alloy or mixed with polymers that can be extruded over the conductive wire 100. Terfenol-D can also be mixed with polymers to form a film, as disclosed in more detail below.

As shown in FIG. 1, the magnetostrictive covering 102 has a certain thickness. The response of the magnetostrictive covering 102 is dependent, at least to some extent, upon the thickness of the magnetostrictive covering 102. In other words, the time response and the amount the magnetostrictive covering 102 change in size depend upon the thickness of the magnetostrictive covering 102.

Figure 2:
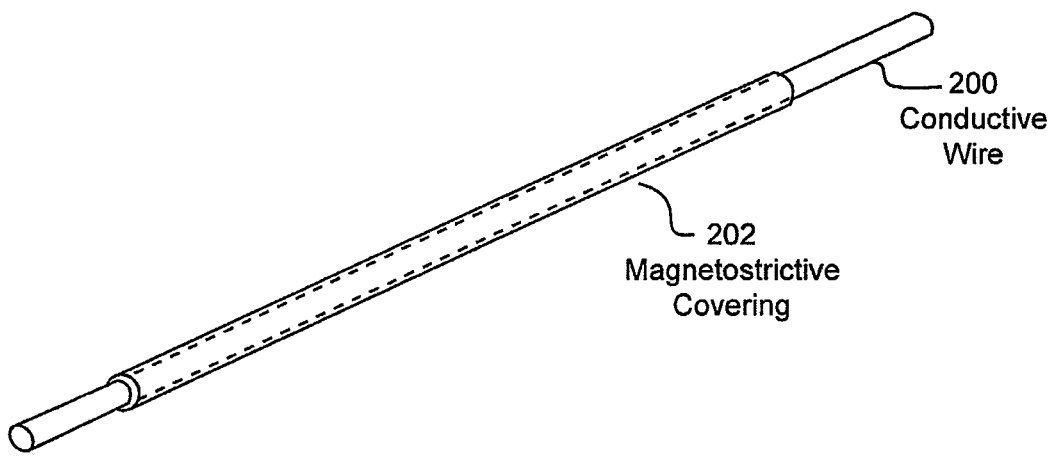
FIG. 2 is a schematic illustration of another embodiment of a conductive wire covered with a magnetostrictive covering.

FIG. 2 illustrates another embodiment of a conductive wire that is covered by a magnetostrictive covering 202. As shown in FIG. 2, the magnetostrictive covering 202 is thinner than the magnetostrictive covering 102 illustrated in FIG. 1. Magnetostrictive covering 202 has a quicker response time than the magnetostrictive covering 102 of FIG. 1 as a result of the fact that the magnetostrictive covering 202 is thinner. The delayed response of the magnetostrictive covering 102 is utilized in accordance with the various embodiments disclosed herein. Layering of 1 mm films can provide 8 mm film which can be effectively used on a diaphragm. Also, any desired thickness of the magnetostrictive material, that is mixed with a polymer, can be extruded directly on a diaphragm. Further, the magnetostrictive material can be mixed with a polymer that is suitable to function as a diaphragm, so that the diaphragm can be extruded or molded with the magnetostrictive material disposed in the diaphragm.

Figure 3:
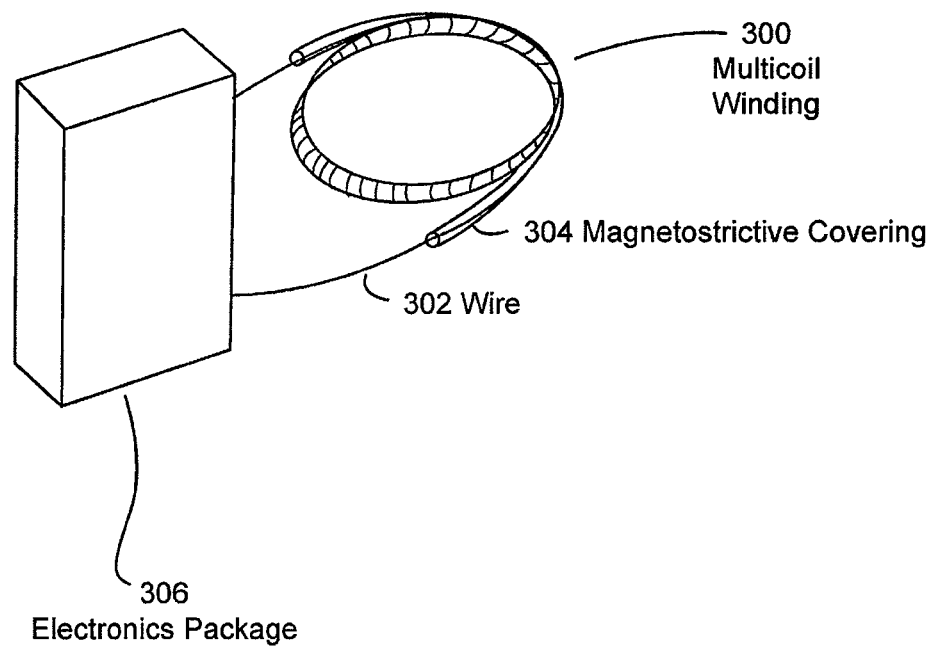
FIG. 3 is a schematic illustration of a multi-coil winding that uses conductive wires having magnetostrictive covering.

FIG. 3 is a schematic illustration of another embodiment. As shown in FIG. 3, a multi-coil winding 300 is made from a wire 302 that is covered with a magnetostrictive covering or coating 304. The magnetostrictive covering 304 reacts to the magnetic field that is created by the current that passes through wire 302, which is applied to the wire 302 by the electronics package 306. Electronics package 306 can include any type of electronics including digital signal processors, microprocessors, active filters, amplifiers, etc. The magnetic field generated by the multi-coil winding 300 causes the magnetostrictive covering 304 to change size. The multi-coil winding 300 with the magnetostrictive coating 304 can be used for hearing devices, as explained more fully below. The advantage of using a conductive wire, such as a copper wire, is that a copper wire, or similar wire, such as a silver wire, has very low resistance and is very efficient in generating a magnetic field. Materials that are magnetizable, such as ferrite based materials, have greater resistance and are therefore less efficient. Because of the small size of most hearing devices, efficiency of the system is important. Very small battery packs must be used in such small devices, which require higher efficiency. Hence, the highly conductive wire, such as a copper wire or a silver wire that is coated with a magnetostrictive material, has the advantage of generating a magnetic filed very efficiently while allowing the magnetostrictive materials to expand and contract to efficiently generate the vibrations that enhance the auditory comprehension of the user.

Magnetostrictive materials, as indicated above, change shape and produce mechanical energy in response to a magnetic field. Conversely, the change in shape of the magnetostrictive material stores energy so that when the magnetostrictive material returns to its original state, it generates a magnetic field that, in turn, will induce current in the coil. In this fashion, use of magnetostrictive material results in the efficient use of energy and minimal drainage of power from the battery. In that regard, changes in the size of the magnetostrictive material can be used to generate electricity and run various types of devices that use electrical energy. For example, the batteries in a hearing aid can be charged using this process.

The number of windings utilized in the multi-coil winding 300 that is illustrated in FIG. 3 affects the magnitude of the magnetic field that is generated by the multi-coil winding 300. It is also believed that the spectral response of the auditory vibrations of the magnetostrictive coating 304 is affected by the number of windings. Hence, a hearing device can be empirically tuned to provide the desired spectral response by changing the number of windings in the coil.

Figure 4:
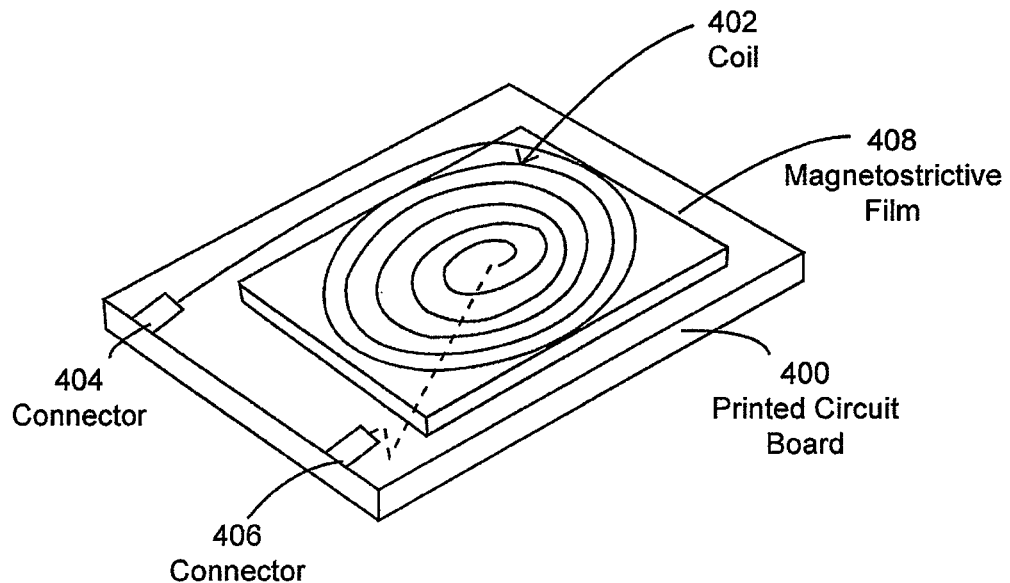
FIG. 4 is a schematic illustration of one embodiment of a printed circuit board device.

FIG. 4 is a schematic illustration of a coil 402 that is disposed on a printed circuit board 400. As shown in FIG. 4, connectors 404, 406 are used to connect to the spiral coil 402. The spiral coil 402 has a spiral shape, rather than a ring shape. In that regard, the term coil is used herein to include both helicoidal as well as ring coils. Electrical connections can be made to the connectors 404, 406 to drive a current through the spiral coil 402. The coil 402 and connectors 404, 406 are printed circuit board traces on the surface of the printed circuit board 400. The current that is applied to the coil 402 causes a magnetic field to be generated that is substantially perpendicular to the coil 402 at the surface of the printed circuit board 400. A magnetostrictive film 408 is placed over the coil 402. The magnetostrictive film may comprise a polymer film that includes a magnetostrictive material such as, but not limited to, Terfenol-D that is mixed with the polymer film. The magnetic field causes the magnetostrictive film 408 to change size in accordance with the frequency of the electrical signal.

Figure 5:
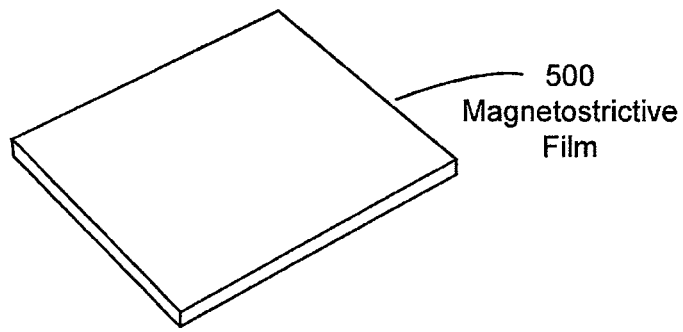
FIG. 5 is a schematic illustration of an embodiment of a magnetostrictive film.

FIG. 5 is a schematic illustration of an embodiment of a magnetostrictive film 500. As shown in FIG. 5, the magnetostrictive film 500 is thin. The magnetostrictive film 500 that is illustrated in FIG. 5 has a rapid response time in response to the magnetic field that is generated by the coil 402.

Figure 6:
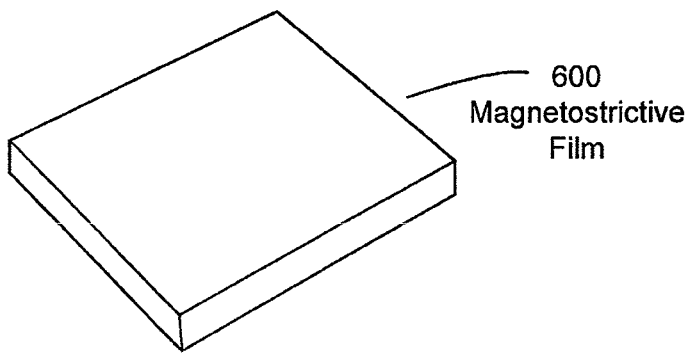
FIG. 6 is a schematic illustration of another embodiment of a magnetostrictive film.

FIG. 6 is an illustration of another embodiment of a magnetostrictive film 600. As shown in FIG. 6, the magnetostrictive film 600 is a thicker film than the magnetostrictive film 500 of FIG. 5. The magnetostrictive film 600 has a slower response time than the magnetostrictive film 500. In other words, there is a delay in the process of causing the magnetostrictive film 600 to change size in response to the magnetic field generated by the coil 402. A thicker coating on coils, traces or wires also may create a longer delay. Hence, a device, such as illustrated in FIG. 4, that uses magnetostrictive film 600 would have a longer response delay compared to a device, such as illustrated in FIG. 4, that uses the thinner magnetostrictive film 500 of FIG. 5.

Figure 7:
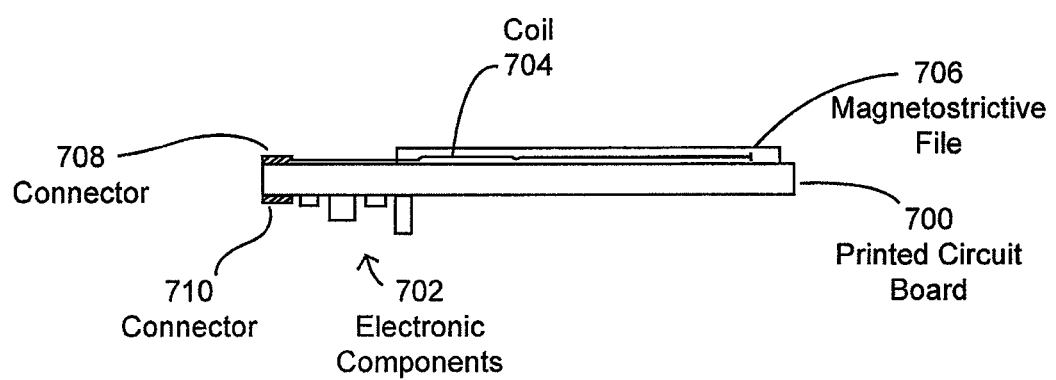
FIG. 7 is a schematic illustration of another embodiment of a printed circuit board device.

FIG. 7 is a schematic illustration of another embodiment that uses a printed circuit board 700 having a coil 704 formed from the printed circuit board leads. As shown in FIG. 7, a magnetostrictive film 706 covers the coil 704. The magnetostrictive film 706 may take various shapes and have various thicknesses when deposited on the printed circuit board. In addition, various mixtures and concentrations of magnetostrictive materials can be used. As also shown in FIG. 7, the electronic components 702 are disposed on an opposite side of the printed circuit board 700. The electronic component 702 can comprise various types of components including active filters, microprocessors, digital signal processors, amplifiers, and any other type of components used in hearing devices. A multi-layer printed circuit board may be used in this application to provide connections on an intermediate layer. Connectors 708, 710 provide connections to a battery pack or other power supply. In this fashion, an electronics package can be provided by the electronic components 706 that are disposed on the printed circuit board 700. Alternatively, the coil 704, magnetostrictive film 706 and the electronic components 702 can be mounted on the same side of the board. In any event, the electronic components 702 are mounted outside of the periphery of the coil 704, so as to minimize interference with the magnetic field that is generated by coil 704. Alternatively, the magnetostrictive film 706, illustrated in FIG. 7, may be deposited on a suspended diaphragm over the coil on the printed circuit board 700 to allow greater movement of the magnetostrictive film 706 and provide greater efficiency in the production of sound waves.

Figure 8:
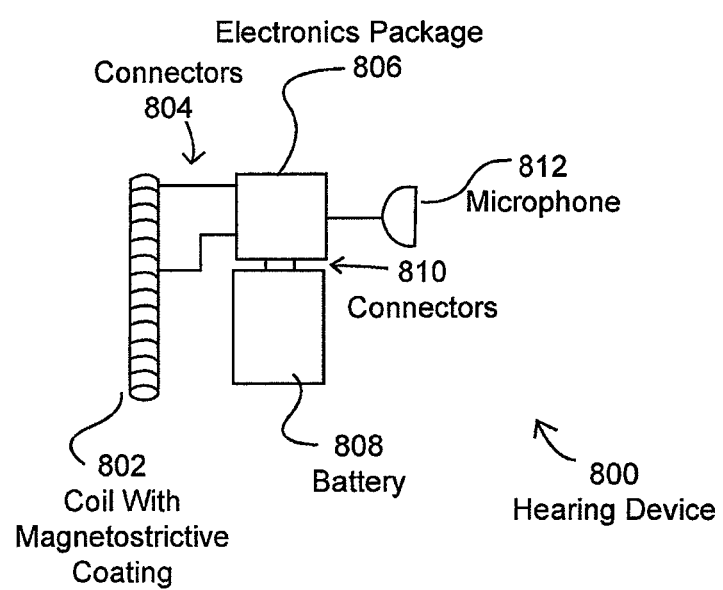
FIG. 8 is a schematic illustration of an embodiment of a hearing device.

FIG. 8 is a schematic illustration of a hearing device 800. The hearing device 800 may comprise a hearing aid or hearing aid receiver, collectively referred to as a hearing device, that can be a miniaturized hearing aid that is disposed either partially within, or fully within, the ear canal of a user. The size of the components allows for construction of the hearing device 800 that can be inserted in the ear canal. In that regard, the simplicity of the construction of the embodiment of FIG. 8 provides for a high degree of miniaturization. Further, the hearing device 800 of FIG. 8 can also be disposed in other types of hearing devices, such as ear phones, telephones, speakers and other types of devices that generate auditory sound waves. As shown in FIG. 8, the coil 802 has a magnetostrictive coating, such as illustrated in FIGS. 1 and 2. Alternatively, the coil 802 may be wrapped with a magnetostrictive film that comprises a magnetostrictive material, such as Terfenol-D, that is impregnated in a polymer or other film material. Coil 802 is connected to the electronics package 806 via connectors 804. Electronics package 806 receives an auditory signal from the microphone 812, which is amplified by the electronics package 806 and applied via connectors 804 to the coil 802. Battery 808 is connected to the electronics package 806 via connectors 810 to provide power to the hearing device 800. The magnetostrictive material efficiently changes shape in response to a magnetic field that is generated by the current that is running through the coil 802. The thickness of the magnetostrictive coating, or the thickness of the film applied around the coil 802, determines the response of the magnetostrictive material to the current that is applied to the coil 802. The current that is applied to the coil 802 generates a magnetic field that varies with the number of coil windings of the coil 802. The auditory vibrations of the coil 802 generate sound and auditory vibrational waves that assist the user in hearing, understanding and enjoying auditory tones. Sound waves and auditory vibrations are efficiently produced in the magnetostrictive material because of the close contact of the magnetostrictive material with the coil 802. In addition, many harmonic frequencies are created because of the efficiency of the magnetostrictive coating in generating auditory vibrations. Again, this is due to the close proximity of the magnetostrictive coating to the wire of the coil 802. For hearing devices that are inserted in the ear canal, the auditory vibrations of the magnetostrictive coating on the coil 802 additionally assist the user in hearing tonal frequencies. A significantly improved hearing response is achieved using the magnetostrictive coating on the coil. The magnetostrictive material tends to create some noise, which may assist the user in hearing, as a result of the stochastic resonance. Stochastic resonance may aid the user in the detection and/or enhancement of the auditory signal for easier hearing, identification and enjoyment of the auditory signal. In addition, Barkhausen noise may also assist the user in hearing. Barkhausen noise is the result of a series of sudden changes in the size and orientation of ferromagnetic domains, or microscopic clusters of aligned atomic magnets, that occurs during a continuous process of magnetization and demagnetization. In other words, magnetization and demagnetization occurs in minute steps. This creates a clicking or crackling noise because of the discontinuous jumps in magnetization. This may assist the user in hearing, as a result of stochastic resonance.

Although inner hair cells are outnumbered approximately four to one by outer hair cells, the inner hair cells gather and transmit the majority of auditory information that reaches the cerebral cortex. Because the cilia of the inner hair cells are not attached to the tectorial membrane, stimulation of the inner hair cells most likely results from motion of the surrounding fluid and basilar membrane. Brownian motion of the inner hair cell bundles may provide an optimal noise level that enhances the sensitivity of the mechanical/electrical transmission to weak acoustic signals. The vibrations provided by the coil 802, as well as the strong magnetic field that is generated by the coil 802, may increase the movement of the fluid in the inner ear, which may increase the firing of the inner hair cells. Therefore, Brownian motion created by the embodiment illustrated in FIG. 8 may serve to provide a greater opportunity for signal transmission in a user's ear that has significant outer hair cell damage and inner hair cells intact. In addition, the coil 802 with the magnetostrictive coating efficiently creates harmonics of the base frequencies that are very beneficial to the enhancement of speech discrimination.

As disclosed in FIGS. 1 and 2, magnetostrictive coatings can be used that have different thicknesses and different phase and time delay responses. The constriction of two different hearing devices 800 can be accomplished using two different thicknesses of magnetostrictive coverings. Different thicknesses can be provided using a different number of layers of magnetostrictive material. In this fashion, a hearing device having the thicker magnetostrictive covering 102 will have a delayed response and a different phase.

Central auditory processing disorder (CAPD) is a condition in which the user has difficulty processing or interpreting auditory information in a less than optimal listening environment. Individuals with CAPD typically have normal hearing acuity, but are unable to efficiently process or interpret speech when placed in a minimally noisy environment. Children and adults with CAPD often report that they are confused or become flustered in busy, listening environments. In classroom environments, the workplace and social gatherings, these individuals often have difficulty and are confused by different verbal stimuli. CAPD may occur in persons with other disorders, such as autism, ADD/ADHD, sensatory integration dysfunction, learning disabilities, speech and language deficients, traumatic brain injury or other neurological conditions. CAPD may also appear as an isolated dysfunction. For children and adults with CAPD, there is evidence of binaural asynchronies (BAs) in their central auditory nervous system (CANS). Binaural asynchronies are synchrony disruptions (delay) in time of auditory input signals to the individual's ears. Efficient processing of acoustic information relies on binaural interaction or synchronization of auditory inputs between the two ears, which is accomplished by the central auditory nervous system in most individuals. For a person with a normal central auditory nervous system function, auditory input between the two ears is synchronized in time. However, for an individual with atypical central nervous system function, there are asynchronies of various magnitudes that hinder efficient auditory processing of acoustic information.

By introducing a delay in the auditory signals that are processed by the hearing device 800 by using different thicknesses of magnetostrictive coverings, binaural asynchronies can be reduced or eliminated, and users can more effectively distinguish and understand auditory signals. This is a result of the fact that the magnetostrictive coverings 102, 202 can be used to introduce a delay in one of the ears, which may assist the user in synchronizing auditory signals. Proper delay by using different thickness of magnetostrictive materials can be established empirically. The delay can also assist users having other neurological disorders, such as traumatic brain injury, Parkinson's disease, multiple sclerosis, etc.

Delay of the sound signal can also be assisted by employing the concepts of the invention in an ear canal device that has a duct that changes the propagation length of the sound for each individual ear. In other words, concepts of the various embodiments may be employed in the ear hearing device such that propagation lengths are different for each ear. Passive delay devices can be used separately or in conjunction with the various embodiments disclosed herein. Passive delay devices are more fully disclosed in U.S. patent application Ser. No. 11/443,859, filed May 31, 2006, entitled "Apparatus and Methods for Mitigating Impairments Due to Central Auditory Nervous System Binaural Phase-Time Asynchrony," which is specifically incorporated herein by reference for all that it discloses and teaches.

Comprehension of auditory signals using hearing devices can be negatively impacted by electromagnetic interference. A multi-coil winding 300, such as shown in FIG. 3, that has a magnetostrictive covering 102, or a magnetostrictive film 408 over a coil 402, as shown in FIG. 4, is believed to reduce electromagnetic interference. For example, appliances that use a large amount of current, such as a computer monitor, television or other similar device, may create interference in a hearing device because of the electromagnetic interference of the electrical power signal applied to the appliance. Many hearing aids are constructed using a moving coil apparatus, or a balanced armature apparatus. Each of these devices may function as antennas that pick up the electromagnetic interference that is converted by the hearing device into an auditory hum that is transmitted to the user's ear. This may also be the case with electrostatic type of drivers that use electrically charged diaphragms. The embodiments disclosed herein are believed to reduce the electromagnetic interference and provide a high spectral response that aids users in hearing auditory signals. Use of magnetostrictive covering on loop systems that interact with a T coil system in a hearing aid or other hearing device, may result in less electromagnetic interference. Another possible source of interference that is encountered in standard hearing devices, and not encountered in the embodiments disclosed herein, is interference from magnetic fields. Many standard hearing devices operate by using a moving coil mechanism in which a moving coil is attached to a diaphragm that is exposed in a static magnetic field generated by a permanent magnet. Variations of the current that is applied to the coil causes the coil to generate a magnetic field that interacts with the static magnetic field and causes the coil to move on the diaphragm. In this fashion, sound waves are produced. Various electronic devices generate magnetic fields that perturb the static magnetic field of the permanent magnet in the hearing device. These perturbations in the static magnetic field create interference in the hearing device. None of the embodiments disclosed herein utilize a static magnetic field that can be perturbed by magnetic fields generated by various electronic devices. As a result, interference by magnetic field waves does not occur in the embodiments disclosed herein.

Figure 9:
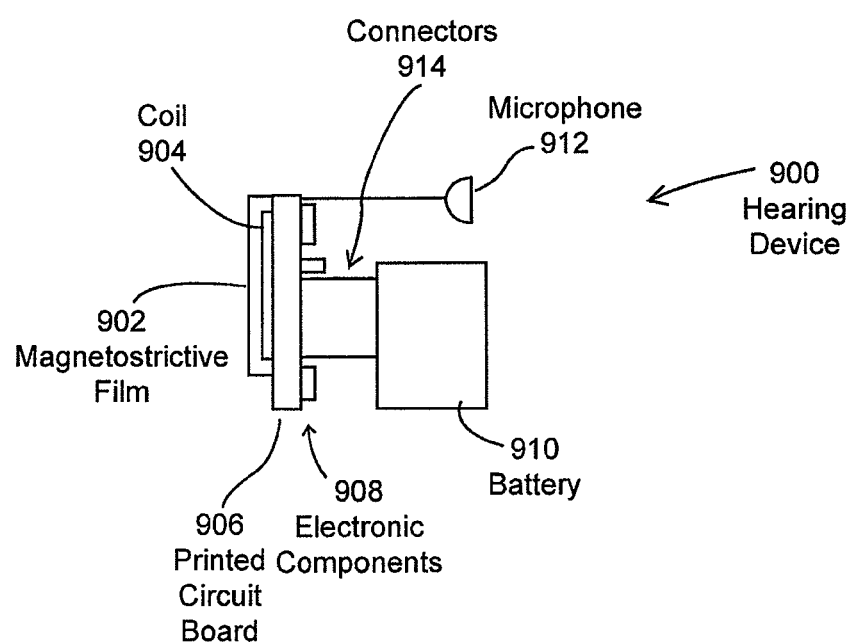
FIG. 9 is a schematic illustration of another embodiment of a hearing device.

FIG. 9 is a schematic illustration of another embodiment of a hearing device 900. Hearing device 900 is a device that is also amenable to miniaturization because of its compact size. As shown in FIG. 9, a magnetostrictive film 902 is deposited over coil 904. Coil 904 is a coil that may be made from the printed circuit board traces of printed circuit board 906. Electronic components 908 may be disposed on the other side of the printed circuit board 906 from coil 904 or on the same side. Electronic components 908 may be disposed around the periphery of the printed circuit board, or to one side of the circuit board, so that the magnetic waves generated by the coil 904 are not interrupted by the electronic components 908. The printed circuit board 906 and the electronic components 908 are connected to a microphone 912 that detects auditory signals. These auditory signals are amplified and applied to the coil 904. Current in the coil 904 generates a magnetic field that causes the magnetostrictive film 902 to change size and generate auditory vibrations. The auditory vibrations of the magnetostrictive film 902 produce sound waves that are efficiently transmitted to the user. In addition, the auditory vibrations of the magnetostrictive film 902 may be transmitted through the tissue in the user's ear to further assist in hearing and comprehension. Battery 910 supplies power to the electronic components 908 on the printed circuit board 906 via connectors 914.

The hearing device 900, illustrated in FIG. 9, may be a hearing aid that is disposed in the outer ear, headphones, a telephone, a speaker or many other types of hearing devices. Since the magnetostrictive film 902 is placed directly over the coil 904, a high degree of efficiency is achieved in generating auditory vibrations. As a result, multiple harmonic frequencies are generated, which also assists the user in comprehending the auditory signals detected by the microphone 912. Of course, some auditory frequencies may be amplified to a greater extent than others, in accordance with the standard practice of designing a hearing device for a particular user. In general, however, the efficient operation and generation of multiple harmonic frequencies, as well as the generation of stochastic resonances by both hearing device 800 and hearing device 900, greatly increases the auditory comprehension, understanding and enjoyment by the user. Of course, the various embodiments disclosed herein can be disposed in any type of hearing device including headphones, speakers, ear pods, etc. and could be used by individuals who do not have hearing loss and do not have hearing comprehension problems, but, rather, like to enjoy an audio response and take full advantage of the attributes of various embodiments disclosed herein. Further, each of the devices disclosed herein can be encapsulated in a standard package for connection to a device such as a headphone, speaker, etc. In that regard, the encapsulated packages can be sold as modular devices that can be employed in any desired fashion, such as any type of hearing device, including hearing aids, headphones, speakers, etc.

Figure 10:
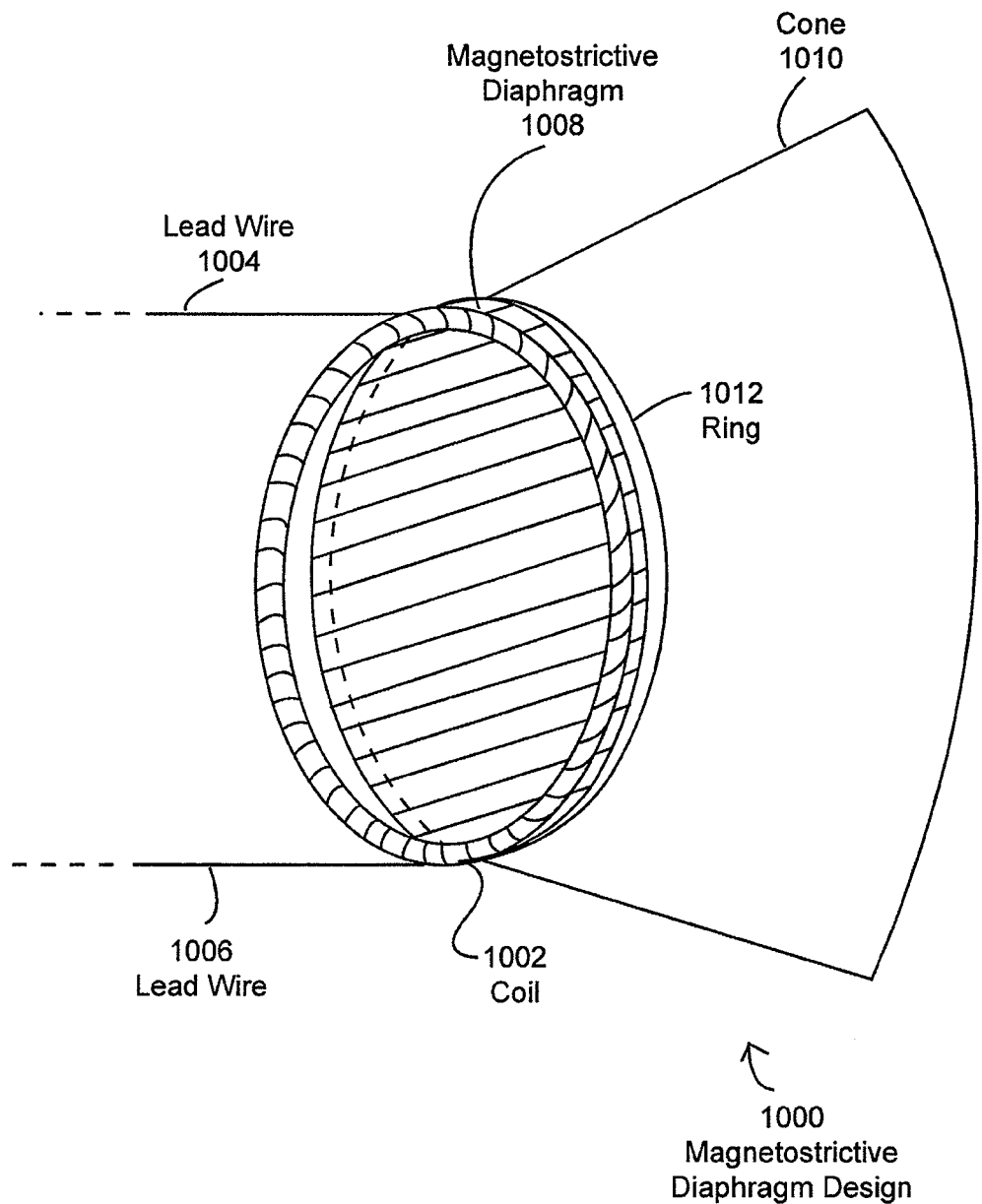
FIG. 10 is a perspective view of another embodiment.
Figure 11:
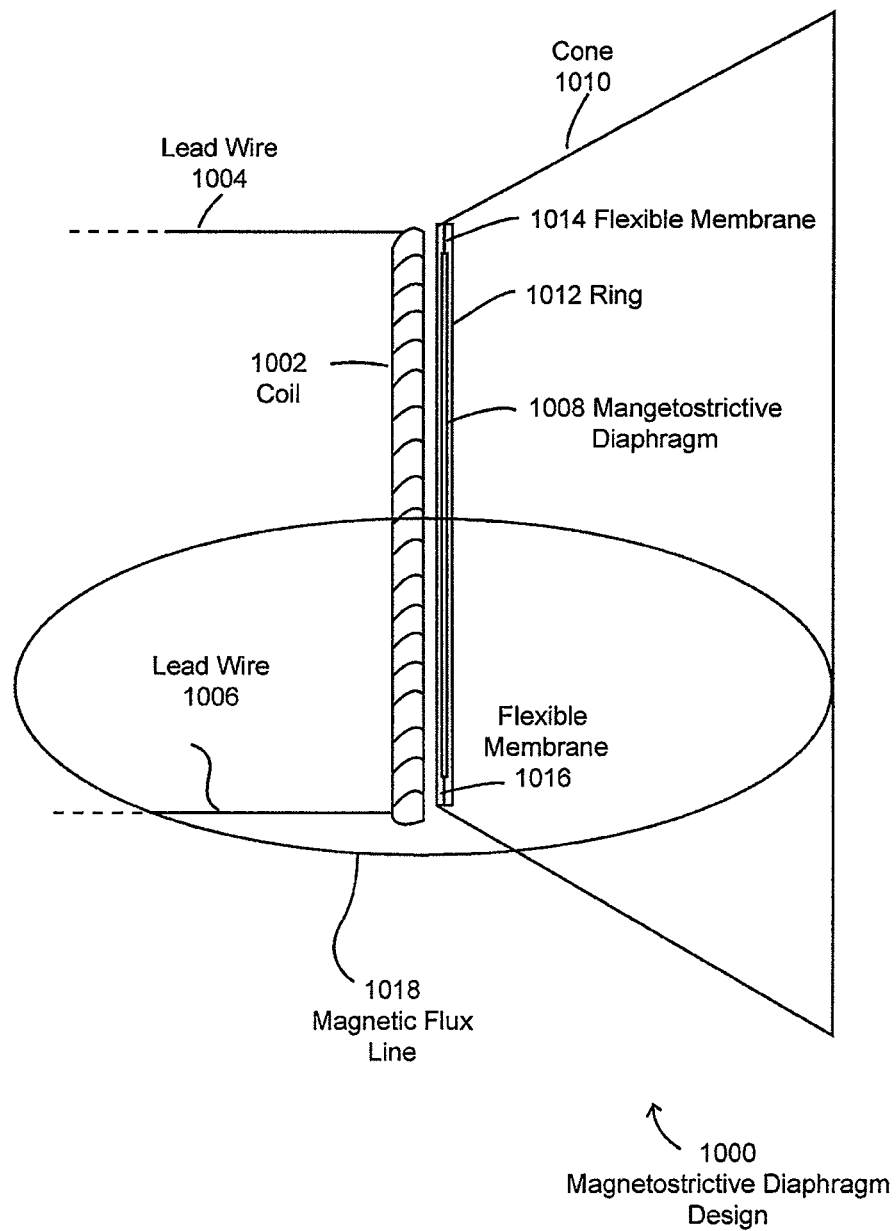
FIG. 11 is a side view of the embodiment of FIG. 10.

FIGS. 10 and 11 disclose a magnetostrictive diaphragm design for hearing devices. FIG. 10 is a perspective view of the magnetostrictive diaphragm design 1000, while FIG. 11 is a side view. As shown in FIG. 10, coil 1002 is attached to lead wires 1004, 1006 that apply electrical signals to the coil 1002 that are representative of auditory signals. The coil 1002 may comprise a conductive wire such as conductive wire 200 that is surrounded by magnetostrictive covering 2002. Alternatively, coil 1002 may be wrapped in a magnetostrictive film or over-molded with a magnetostrictive plastic over-molding. Further, coil 1002 may contain no magnetostrictive materials. Coil 1002 is placed adjacent a ring 1012, as disclosed in both FIGS. 10 and 11. Ring 1012 is a support ring that supports a magnetostrictive diaphragm 1008 that is suspended from the ring by a flexible membrane 1014. Magnetostrictive diaphragm 1008 can be formed from a thin polymer or plastic material that is embedded or mixed with magnetostrictive materials. Cone 1010 is an optional feature that can be used to direct the audio signals that are generated by the magnetostrictive diaphragm 1002.

In operation, the coil 1002 of FIGS. 10 and 11 generates a magnetic field that varies with the application of the electrical signal that is applied to lead wires 1004, 1006. The magnetic field penetrates the coil and the magnetostrictive diaphragm 1008 as shown by the exemplary magnetic flux line 1018. As the magnetic field generated by the coil 1008 varies in response to the electrical signal applied to lead wires 1002, 1006, the magnetostrictive materials change size which causes diaphragm 1008 to move and push the surrounding air to create sound waves. In other words, the magnetostrictive diaphragm 1008 includes magnetostrictive materials that change size in the magnetic field created by the coil 1002 and cause the magnetostrictive diaphragm 1008 to move response to the magnetic field. In addition, Ferrofluid, which is produced by Ferrotec Corporation, can also be coated on the magnetostrictive diaphragm 1008 to further assist in driving the magnetostrictive diaphragm 1008. Ferrofluid is available from Ferrotec Corporation located in Bedford, N.H., and San Jose, Calif.

Figure 12:
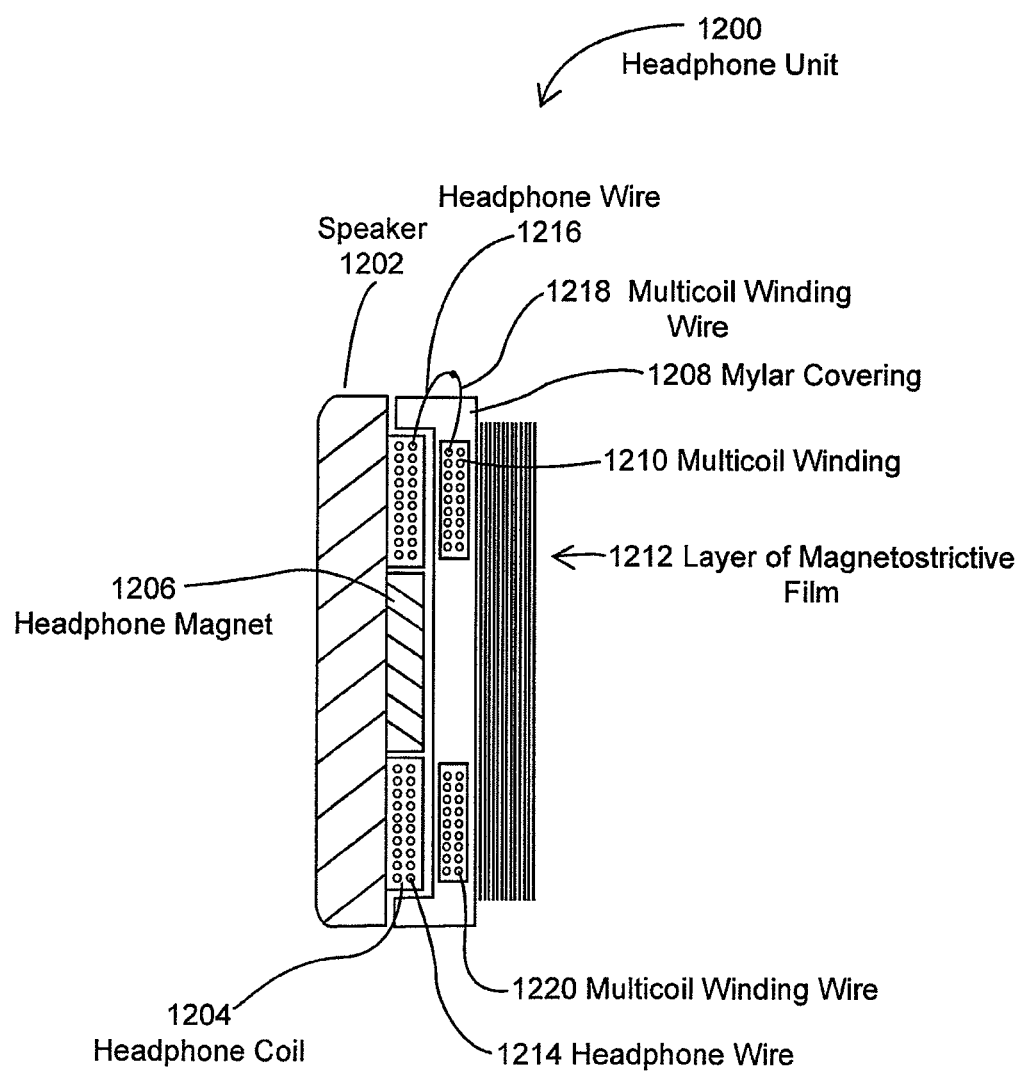
FIG. 12 is a cutaway view of another embodiment.

FIG. 12 is a cutaway view of an embodiment of a headphone unit 1200. As shown in FIG. 12, the headphone unit 1200 includes a speaker 1202, a headphone coil 1204 and a headphone magnet 1206. These are the standard components that are found in typical headphones. As also shown in FIG. 12, a multicoil winding 1210 is embedded in a mylar covering 1208 and placed over the rear portion of the headphone unit adjacent the headphone magnet 1206 and the headphone coil 1204. The mylar covering 1208 can be friction fit to the back of the headphone unit or can be attached by other mechanical means, such as by adhesives, etc. A plurality of layers of magnetostrictive film 1212 are then placed over the mylar covering 1208 and the multicoil winding 1210. The magnetostrictive film may comprise a polymer that is mixed with particles of magnetostrictive material. In one embodiment, each layer of magnetostrictive film has a thickness of 1 mil. The headphone wire 1216 that is attached to the headphone coil 1204 can be clipped and attached to multicoil winding wire 1218. Multicoil winding wire 1220, which is at the other end of the multicoil winding 1210, can then be connected to the drive source for the headphone unit 1200. The headphone wire 1214, which is at the other end of the headphone coil 1204, can remain attached to the driving source. In this manner, multicoil winding 1210 is placed in series with the headphone coil 1204.

The headphone unit 1200 that is illustrated in FIG. 12 provides excellent speech discrimination for both hearing impaired users and users with no hearing loss. Tests on similar headphones are described below, which show increased speech discrimination using similarly modified headphone units. Of course, any type of auditory speaker system can be modified in this manner, including headphones that are used in telephones, ear pods, hearing aids, speakers and similar devices. The multiple layers of magnetostrictive film 1212 also assist in blocking electromagnetic interference, which may be generated by noisy appliances, computers, cell phones, etc.

Tests were performed using headphones that have been modified by placing a magnetostrictive polymer film over the headphone coil similar to the embodiment of FIG. 12. Groove headphones, model TM-707v, available from Groove Industries Co. Ltd, Rm703 A, Huangdu Plaza, Yitian Rd, Futian, Shenzhen, China, were modified to determine speech discrimination. The ear assembly cover of the headphone was pried open to expose the speaker assembly. A circle of thin black foam padding was removed and eight pieces of 1 MIL amorphous magnetostrictive film, that were cut into $^{11}/_{16}$" squares, were stacked together and enclosed with electrical tape. The stacked pieces were then tapes to the speaker assembly of the headphone with a metal assembly placed on top of the tape strip. A 100 turn, 36 G wire coil assembly was then placed on top of the metal layers. The red wire from the speaker was then removed and one end of the coil was attached to the speaker where the red wire was removed. The other coil wire was then attached to the red wire that was removed from the speaker. The earpiece assembly was then reassembled and the other earpiece was modified in the same manner.

Subjects were tested to determine potential benefit from the retrofitted headphones. Speech discrimination measurements were made with both the modified headphones and unmodified headphones in both quiet and noisy environments. One of the most challenging areas for audio and assistive devices for those with hearing loss involves the enhancement of speech understanding in the presence of noise. Understanding speech in noise continues to be the most prevalent complaint of individuals using hearing aids. Designing affordable and easily embedded technology in various audio systems, such as headphones, telephones and hearing aids to address enhancement of speech understanding in noisy environments provides great assistance to many individuals.

The subjects in the testing of the modified headphones were 75 native English speaking male and female subjects from eight years to adult. Participants were recruited from Northern Colorado. The 75 participants were broken into the following groups: 1) normal hearing; 2) hearing loss; 3) central auditory processing disorder. All participants were separated into these groups based upon their pure tone findings and, for those included in the central auditory processing disorder group, by simple auditory processing testing. Participants with hearing loss had hearing thresholds span levels of impairment from a mild degree through profound. Various types of hearing loss and configurations of impairment were included in the study.

The participants were evaluated using strict audiologic controls. All audiologic testing procedures were conducted in a double walled, IAC, soundproof room. A Grason-Stadler (GSI-61) diagnostic audiometer was used to present test items to participants via TDH-50 electrodynamic earphones (10 ohm, mounted in MX/41 AR cushions). The audiometer was calibrated in accordance with ANSI (1989 S3.6) specifications before the collection of data. Speech stimuli for monosyllabic word testing was played on a CD player and passed through the speech circuit of the GSI-61 diagnostic audiometer. Speech reception thresholds (SRT) were established using the W-1 CID Spondee word list, and speech discrimination scores in quiet were obtained using Campbell's word lists. Campbell's word lists are standardized and are commonly used in auditory studies. The pattern of each monosyllabic word was of the consonant-vowel-consonant type. Impedance audiometry was also performed using the Grason-Stadler, Model TympStar impedance unit. Tympanometry was administered for both ears. Three targeted headphones (TH-50 Groove, Model 707 non-retrofitted headphone, Groove, Model 707 retrofitted headphone) were introduced during the final phase of testing. These included standard diagnostic TDH-50 headphones, Groove, Model 707, headphones and Groove, Model 707, retrofitted headphones with new hearing technology. All headphones were calibrated according to ISO (1964) and ANSI (1969) standards. Correction factors were employed throughout testing for each headphone to maintain consistency in output for all headphones and test stimuli. NU-6 phonetically balances word list (Tillman & Carhart 1966) (Lists A1, A2, A4, B1, B2 and B4) were used to determine single words speech discrimination scores in noise. These words were presented via a CD player using a CD recorded by Auditec of St. Louis. Words were presented through the targeted headphones via the Grason-Stadler, Model GSI-61, diagnostic audiometer. These words were presented at 40 dB SL re pure tone average with signal-to-noise ratio of +6 using speech band noise presented ipsilaterally. These word lists are standardized and are commonly used in auditory studies. The pattern of each monosyllabic word was of the consonant-vowel-consonant type. Results of this testing are shown in FIGS. 13 and 14.

Figure 13:
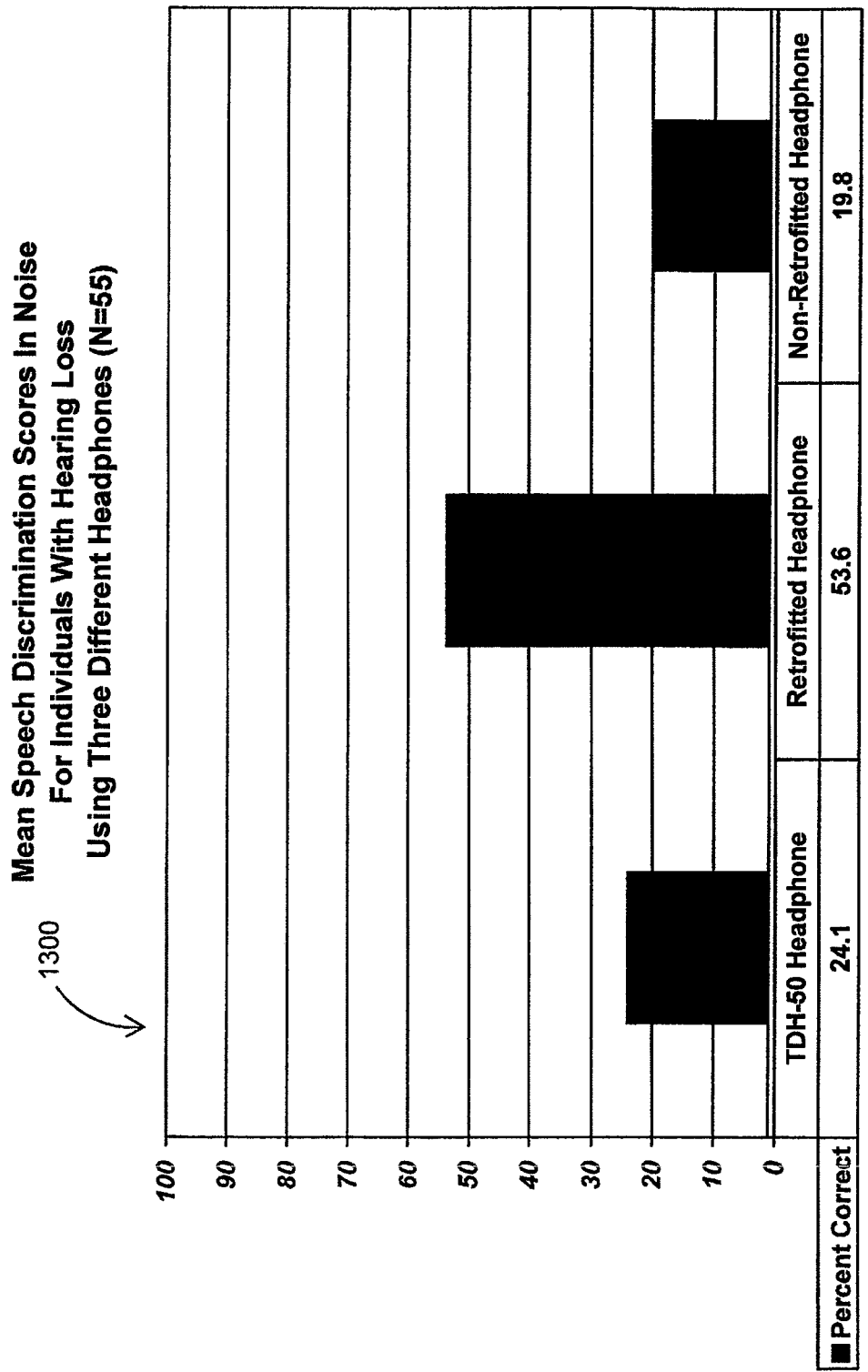
FIGS. 13-24 are graphs of test results.

FIG. 13 discloses a graph 1300 of the mean speech discrimination scores in noise for individuals with hearing loss using three different headphones. As shown in FIG. 13, the retrofitted headphones provided much better speech discrimination.

Figure 14:
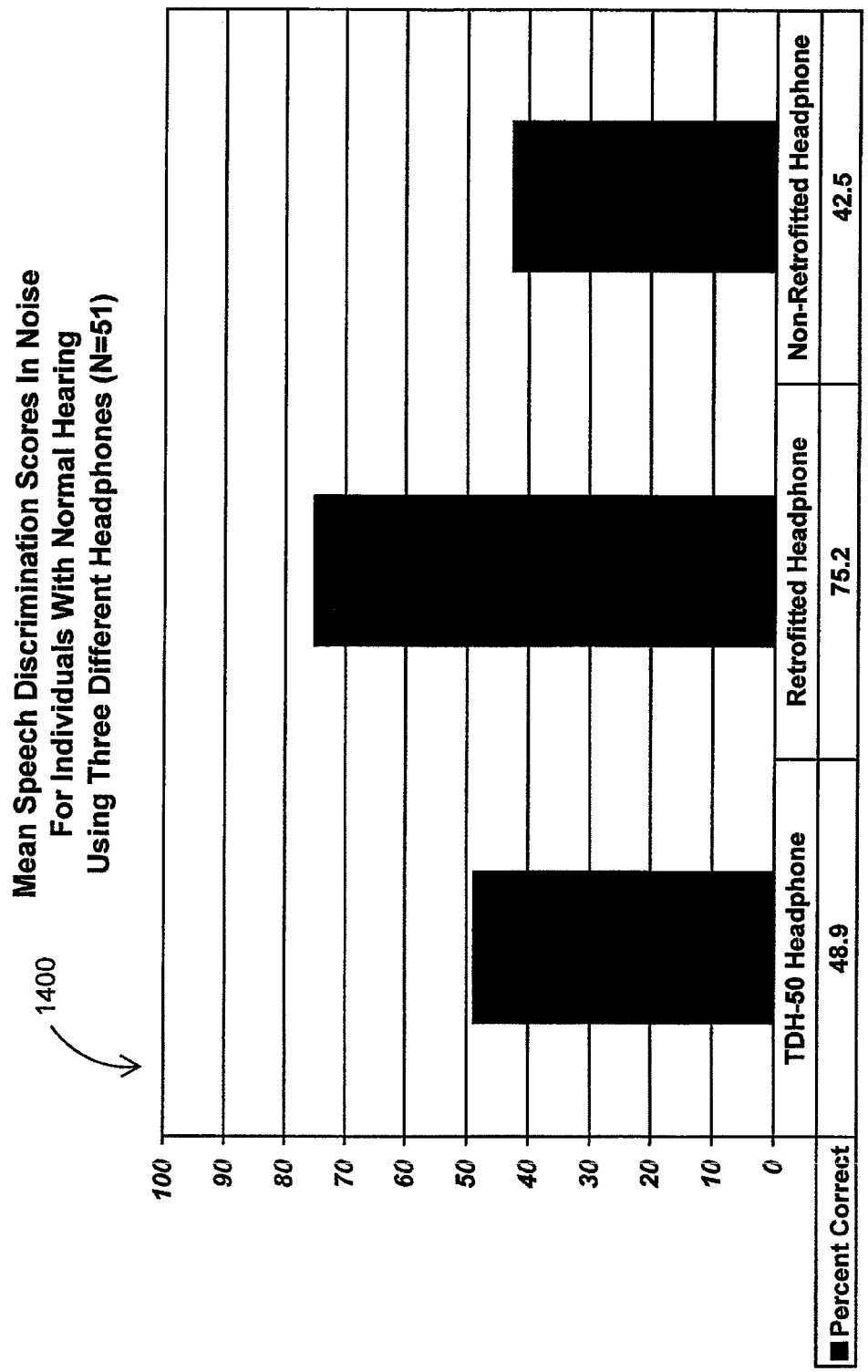

FIG. 14 is a graph 1400 of the mean speech discrimination scores in noise for individuals with normal hearing using three different headphones. As shown in FIG. 14, the retrofitted headphones provided much greater speech discrimination for users with normal hearing.

Figure 15:
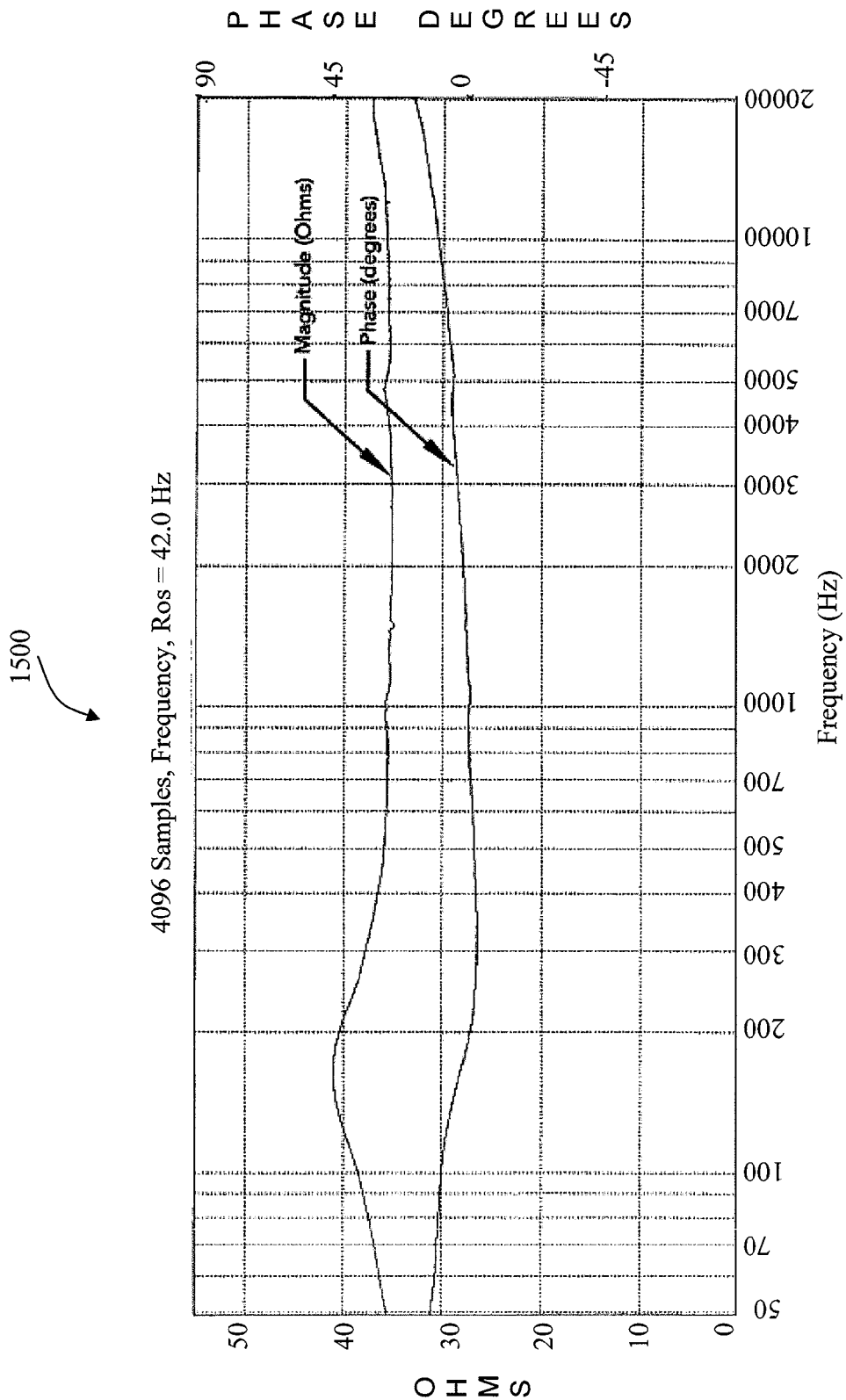
Figure 16:
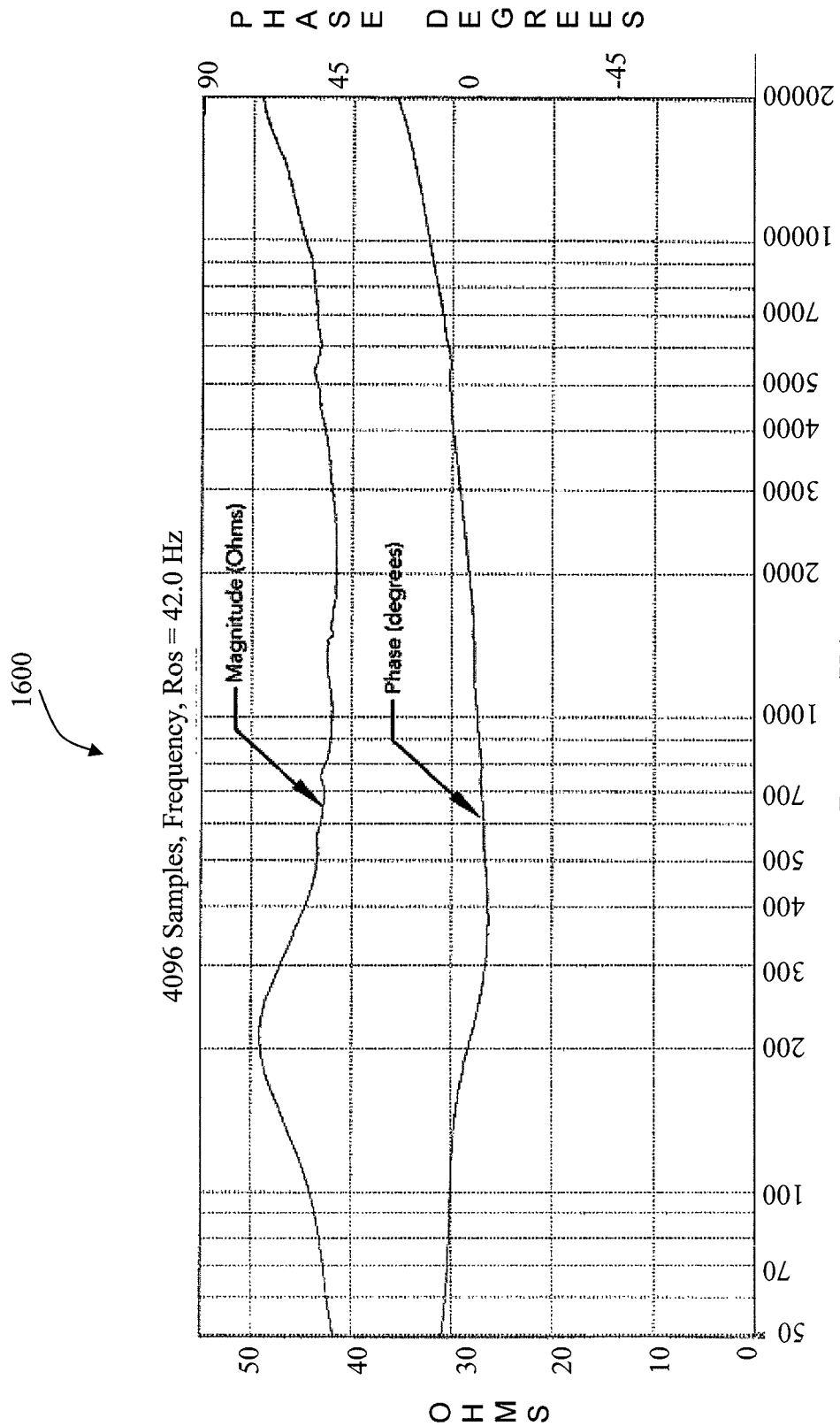
Figure 17:
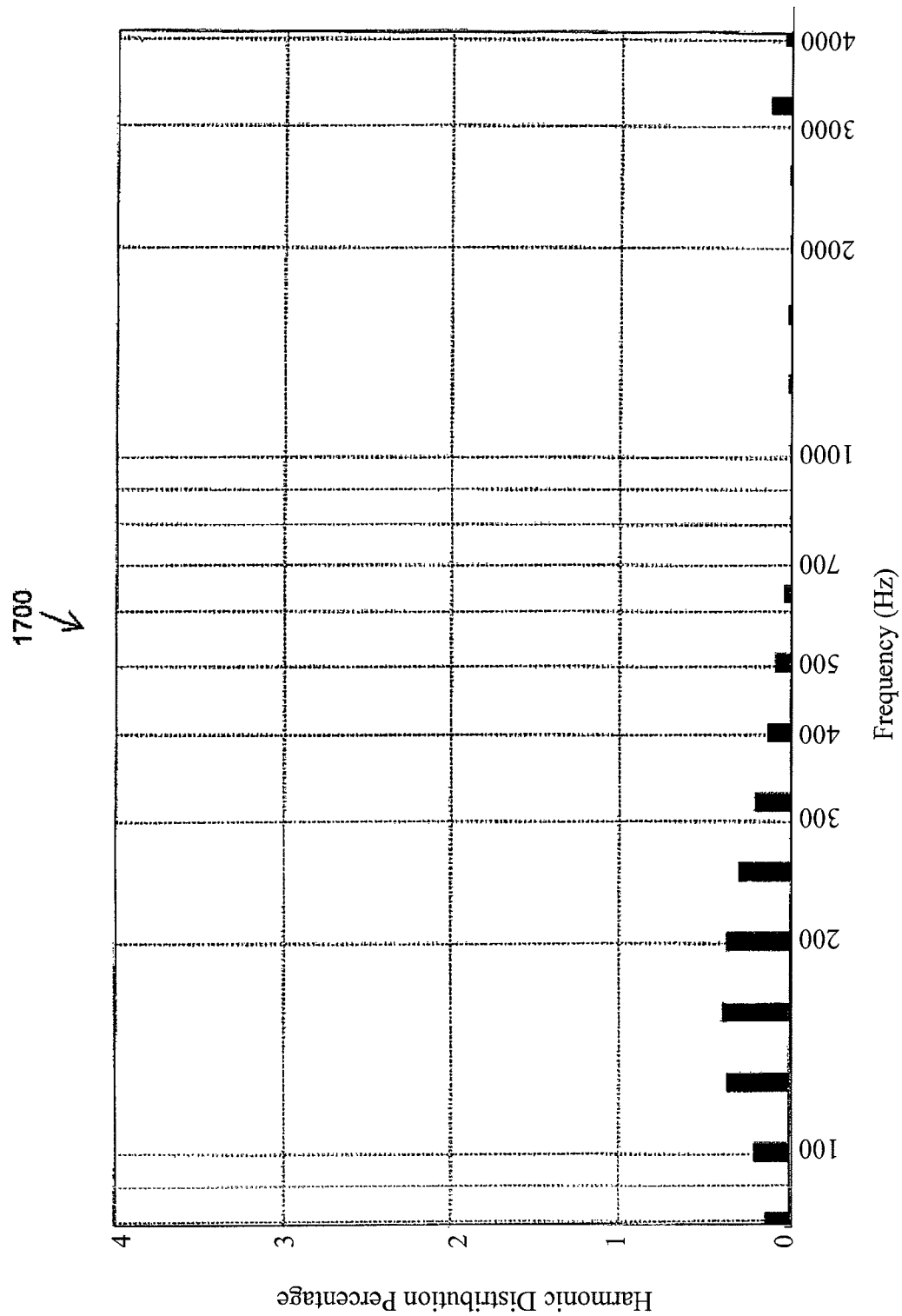
Figure 18:
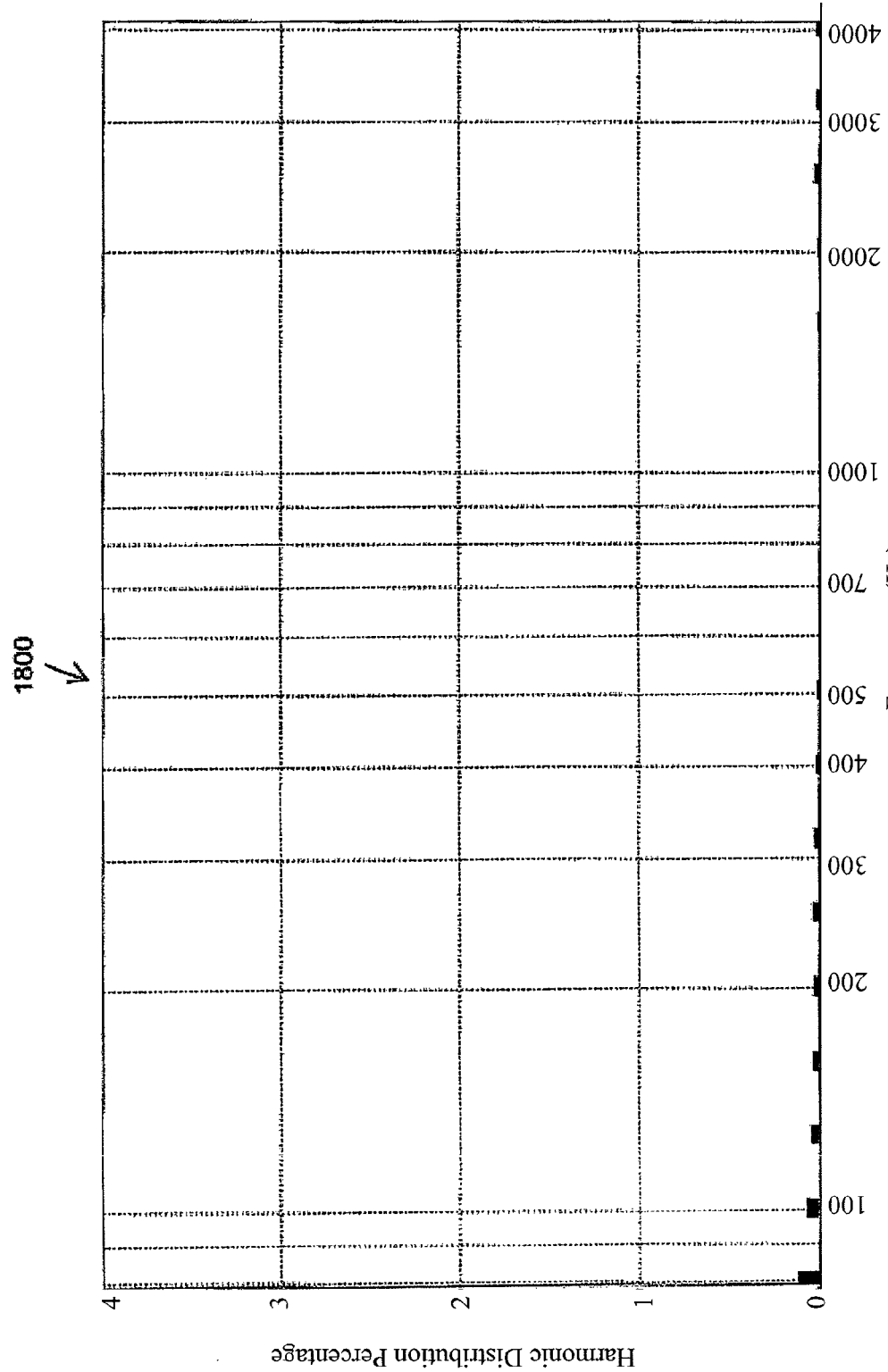
Figure 19:
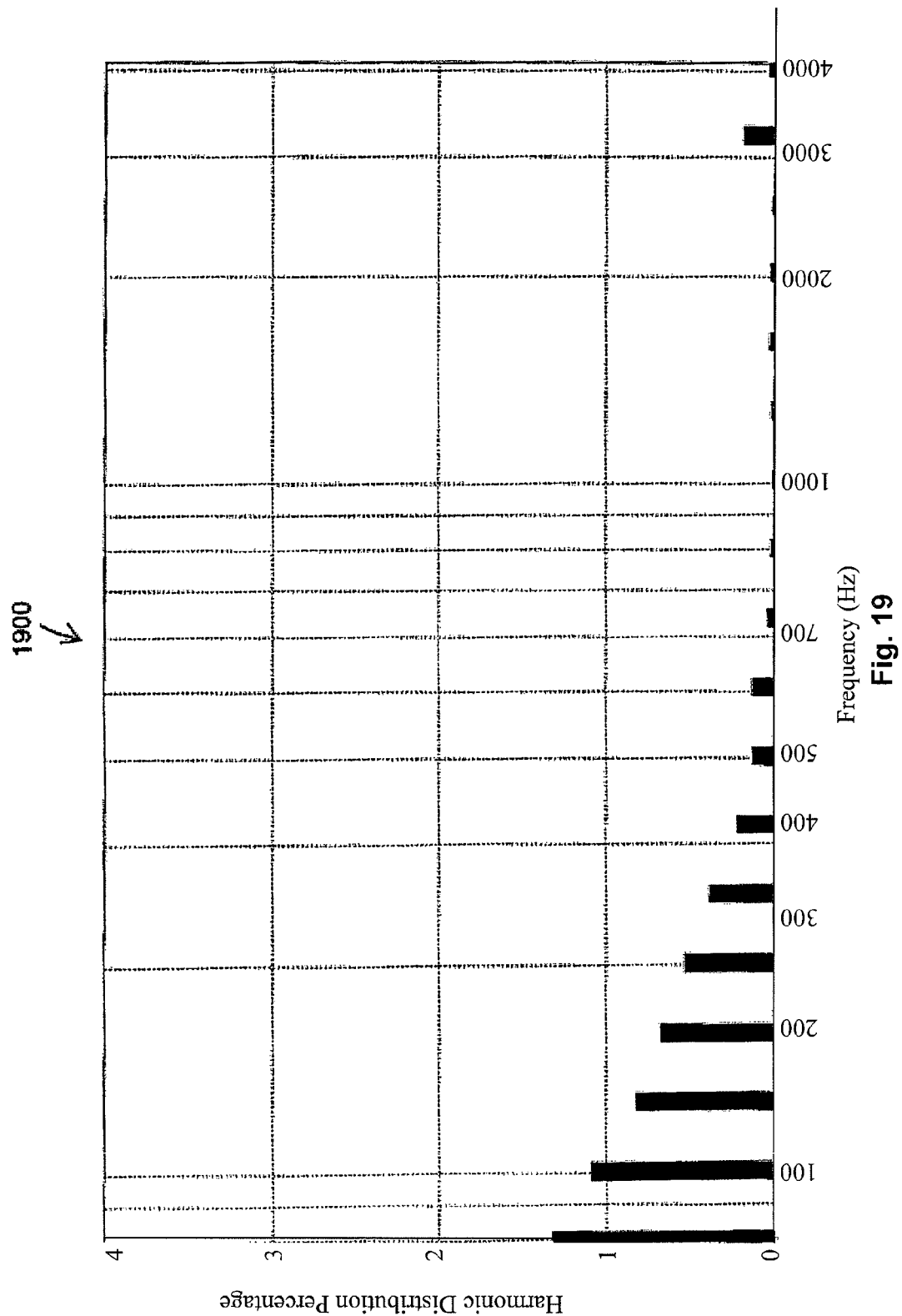
Figure 20:
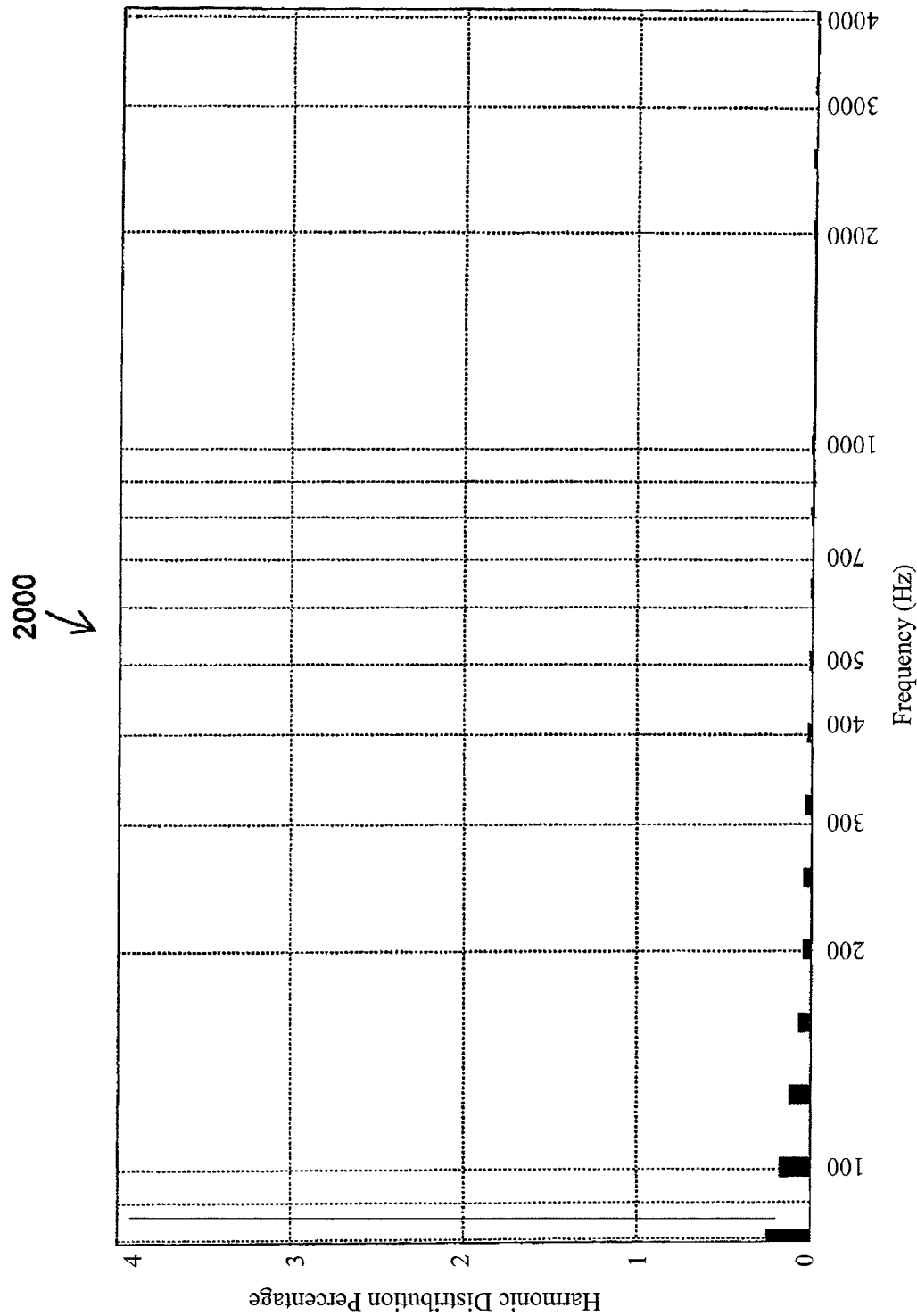
Figure 21:
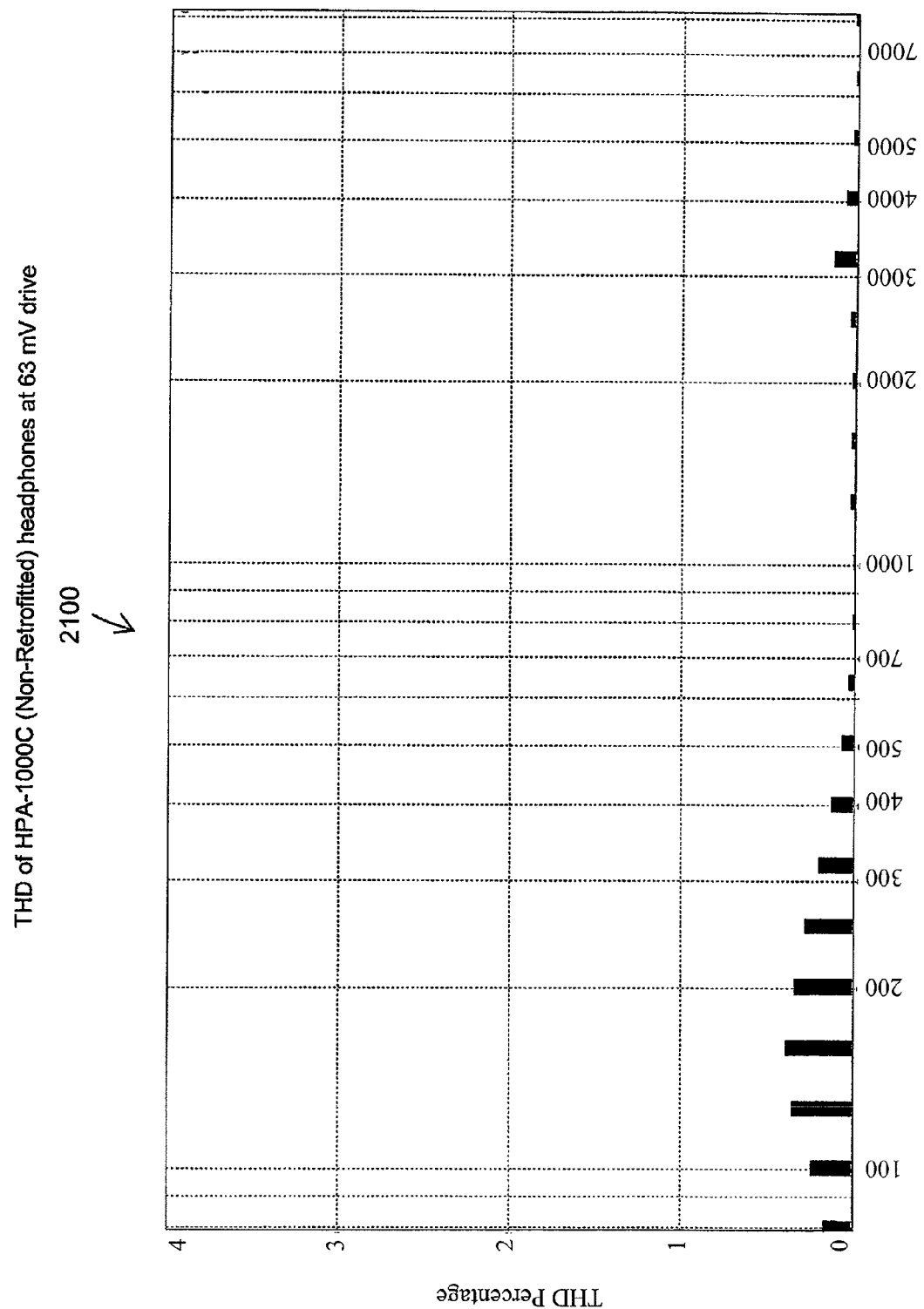
Figure 22:
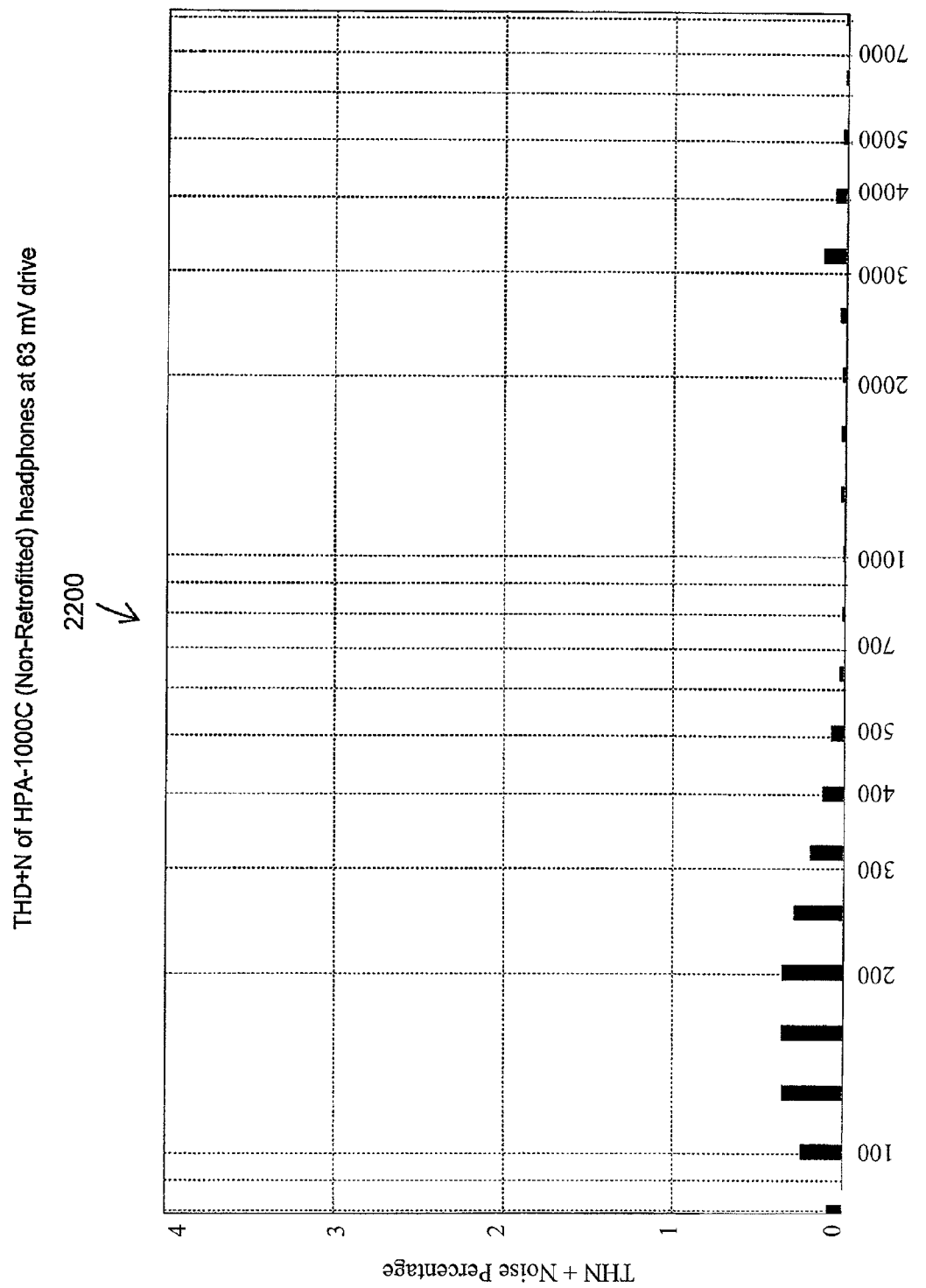
Figure 23:
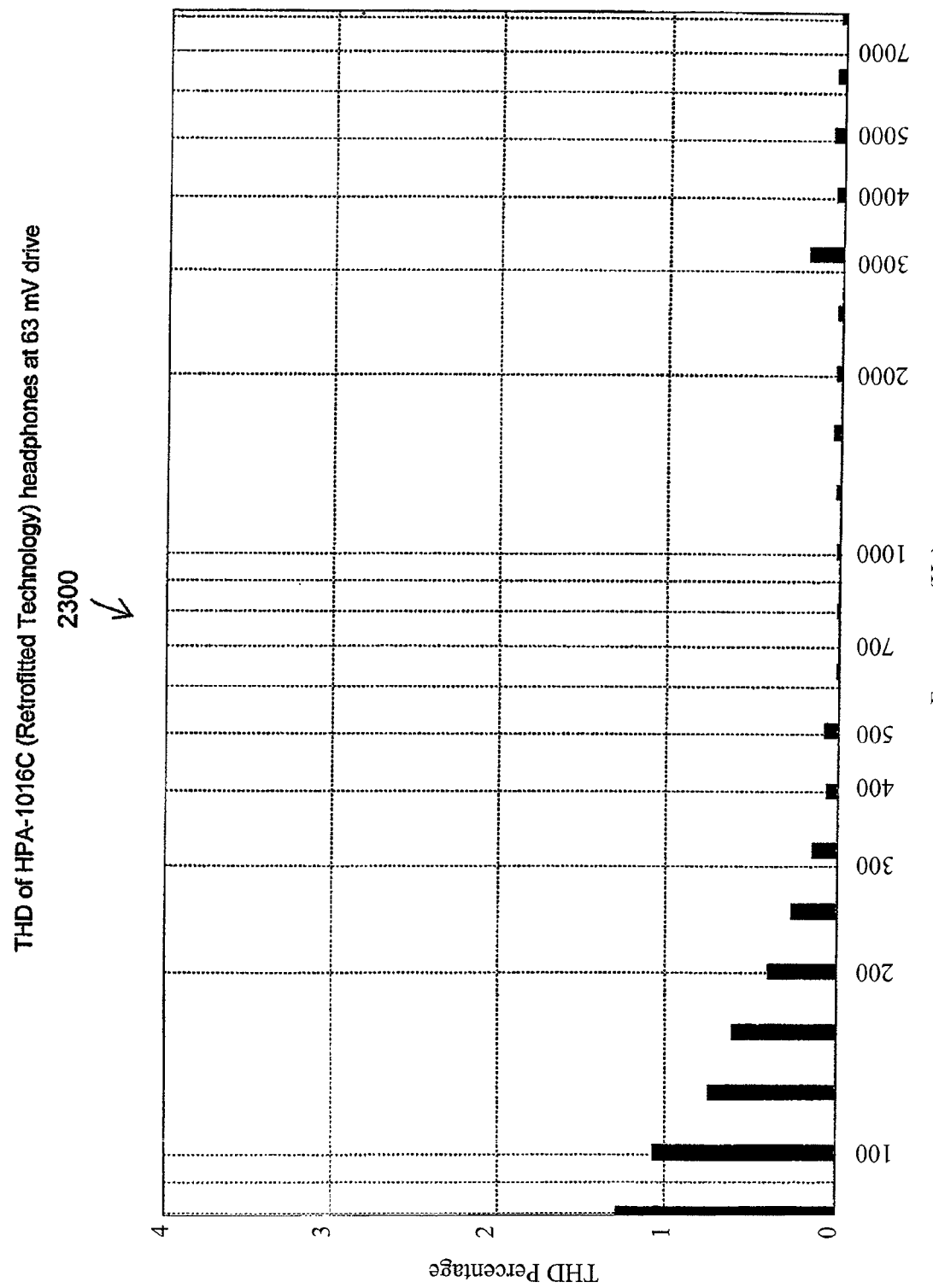
Figure 24:
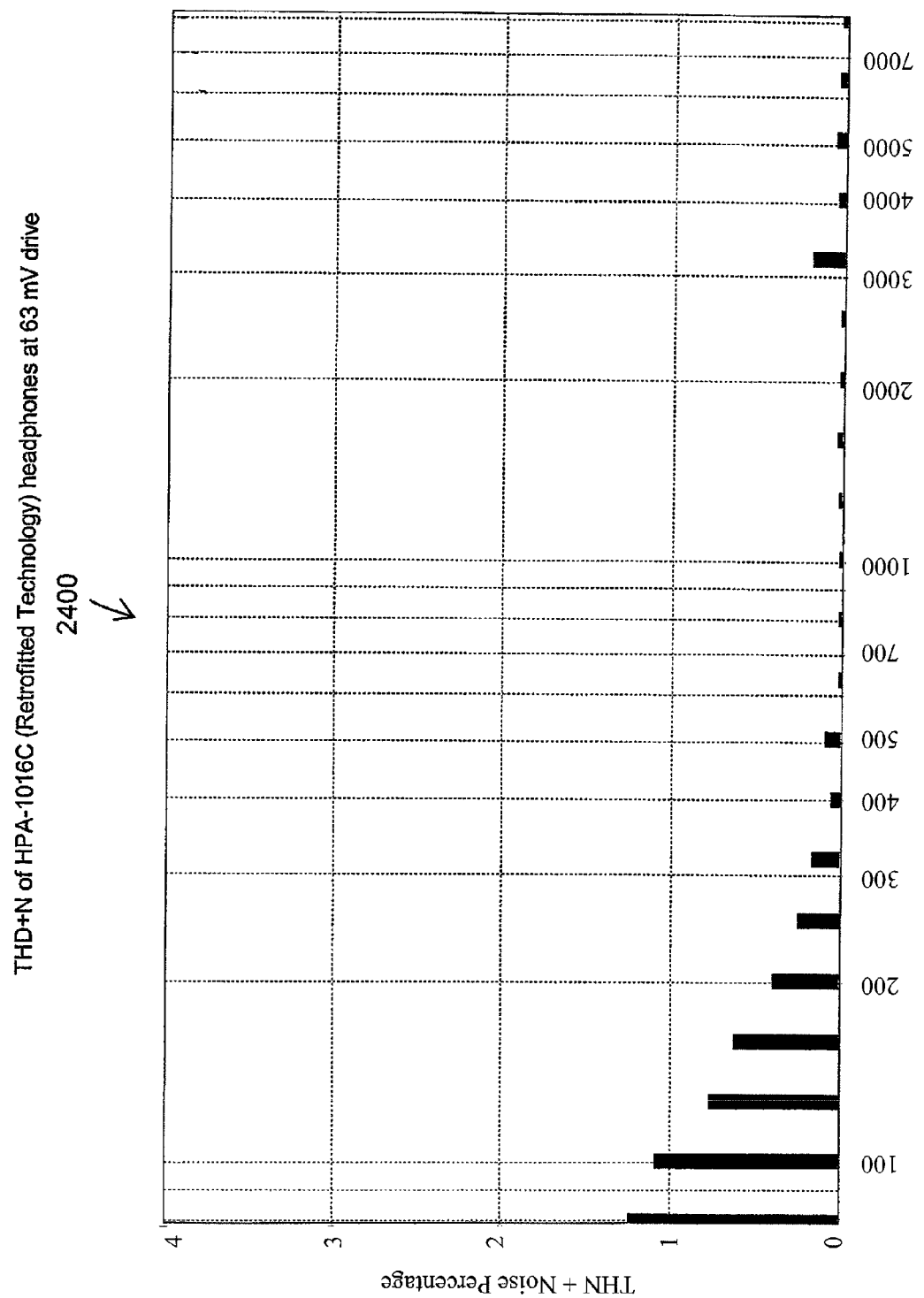

FIGS. 15-24 are graphs of additional test results on the HPA-1000C non-retrofitted headphone and the HPA-1016C retrofitted headphone. FIGS. 15 and 16 show impedance measurements of the headphones versus frequency. FIG. 15 is a graph 1500 of the impedance of an HPA-1000C headphone that is not retrofitted. FIG. 16 is a graph 1600 of the impedance of an HPA-1016C headphone with the retrofitted technology. The impedance measurements are of interest since these graphs show how much of a load each headphone places on the circuit driving the headphone. The lower the impedance of the headphone, the greater the load on the driving circuit. FIG. 17 is a graph 1700 that shows the second and fourth even order harmonic distortion of the HPA-1000C headphones that have not been retrofitted using a 63 mV drive. FIG. 18 is a graph 1800 that shows the third and fifth odd order harmonic distortions of the HPA-1000C non-retrofitted headphones using a 63 mV drive. FIG. 19 is a graph 1900 that shows the second and fourth even order distortion of the HPA-1016C retrofitted headphones, using a 63 mV drive. As shown in FIG. 19, the harmonic distortion of the even orders is much greater for the retrofitted headphones than the even order distortion illustrated in FIG. 17. FIG. 20 is a graph 2000 that shows the third and fifth odd order harmonic distortion of the HPA-1016C retrofitted headphones using a 63 mV drive. FIG. 20 shows much larger harmonic distortions for the retrofitted headphones than the non-retrofitted headphones, for the third and fifth odd order harmonics, illustrated in FIG. 18. FIG. 21 is a graph 2100 of the total harmonic distortion of the HPA-1000C non-retrofitted headphones using a 63 mV drive. FIG. 22 is a graph 2200 of the total harmonic distortion plus noise of the HPA-1000C non-retrofitted headphones using a 63 mV drive. FIG. 23 is a graph 2300 of the total harmonic distortion of the HPA-1016C retrofitted headphones using a 63 mV drive. As shown in FIG. 23, there is substantially greater total harmonic distortion of the retrofitted headphones than that illustrated in FIG. 21, especially at lower frequencies. FIG. 24 is a graph 2400 of the total harmonic distortion plus noise of the HPA-1016C retrofitted headphones using a 63 mV drive. Again, there is a substantially larger amount of total harmonic distortion illustrated in FIG. 24, as compared to that shown in FIG. 22, especially at lower frequencies. Hence, these tests illustrate that harmonic distortion is increased with the modified headphones which may assist in the process of speech discrimination. All of the measurements were made with a gold-Line TEF 25 analyzer. Level calibration was performed by a Bruel & Kjaer 4231 calibrator. Acoustic measurement was performed by a General Radio (GenRad) 1560-T83 earphone coupler with a 1987-2050 adapter. The microphone used was a Sound First SF111 Type 1 microphone. The headphones were driven by a Whirlwind PA-1 headphone amplifier set for unity gain. The headphone amplifier has an output impedance of 10 ohms.

The foregoing description of the invention has been presented for purposes of illustration and description. It is not intended to be exhaustive or to limit the invention to the precise form disclosed, and other modifications and variaions may be possible in light of the above teachings. The embodiment was chosen and described in order to best explain the principles of the invention and its practical application to thereby enable others skilled in the art to best utilize the invention in various embodiments and various modifications as are suited to the particular use contemplated. It is intended that the appended claims be construed to include other alternative embodiments of the invention except insofar as limited by the prior art.

What is claimed is:

1. A method of assisting an individual with auditory comprehension of audible signals using a hearing device comprising:
    providing a coil from a printed circuit board trace on a printed circuit board;
    providing a magnetostrictive film that covers said coil that is formed on said printed circuit board;
    generating an electrical signal from said auditory signal;
    applying said electrical signal to said coil that causes said magnetostrictive film to change size in response to said electrical signal so that said magnetostrictive film generates auditory vibrations to assist said individual with said auditory comprehension of audible signals.

2. The method of claim 1 further comprising:
    providing a second hearing device for another ear of said individual;
    providing a second magnetostrictive film that has a second thickness that is different from a thickness of said magnetostrictive coating that covers a second coil on a second printed circuit board of said second hearing device so that said second hearing device has a different response time that assists said individual in comprehension of said audible signals.

3. A hearing device that assists users having impaired auditory comprehension comprising:
    a detector that receives auditory signals and translates said auditory signals into an electrical signal that varies in amplitude in accordance with said auditory signals;
    a driver that amplifies said electrical signal to provide an amplified electrical signal;
    a coil formed from a printed circuit board trace on a printed circuit board;
    a first magnetostrictive film substantially covering said coil on said printed circuit board that changes size in response to a magnetic field generated by said amplified electrical signal that is applied to said coil and generates auditory vibrations corresponding to said amplitude of said amplified electrical signal that assist said users in comprehending said audible signals.

4. The hearing device of claim 3 further comprising:
    a second hearing device that has a second magnetostrictive film that is thicker than said first magnetostrictive film so that said second hearing device has a delayed response to assist users, having CAPD and/or other neurological disorders, in comprehending said audible signals.

5. A method of assisting an individual with hearing auditory signals using a hearing device comprising:
    providing a coil from a printed circuit board trace on a printed circuit board;
    providing a magnetostrictive film that covers said coil that is formed on said printed circuit board;
    generating an electrical signal from said auditory signal;
    applying said electrical signal to said coil that causes said magnetostrictive film to change size in response to said electrical signal so that said magnetostrictive film generates auditory vibrations to assist said individuals with hearing said auditory signals.

6. The method of claim 5 wherein interference of electromagnetic waves is reduced.

7. A hearing device that assists users having impaired hearing comprising:
    a detector that detects auditory signals and translates said auditory signals into an electrical signal that varies in amplitude in accordance with said auditory signals;
    a driver that amplifies said electrical signal to provide an amplified electrical signal;
    a coil formed from a printed circuit board trace on a printed circuit board;
    a magnetostrictive film substantially covering said coil on said printed circuit board that changes size in response to a magnetic field generated by said amplified electrical signal that is applied to said coil and generates auditory vibrations corresponding to said amplitude of said amplified electrical signal that assist said users in hearing said auditory signals.

8. The hearing device of claim 7 wherein electromagnetic interference is reduced by said hearing device.

* * * * *